US011523986B2

(12) United States Patent
Sramek et al.

(10) Patent No.: US 11,523,986 B2
(45) Date of Patent: *Dec. 13, 2022

(54) INTRANASALLY ADMINISTERED ANTIHISTAMINES AND USES THEREOF

(71) Applicant: DBBH, LLC, Beverly Hills, CA (US)

(72) Inventors: John Sramek, Oxnard, CA (US); Anthony R. DiSanto, Gobles, MI (US)

(73) Assignee: DBBH, LLC, Beverly Hills, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/823,835

(22) Filed: Mar. 19, 2020

(65) Prior Publication Data

US 2020/0297623 A1 Sep. 24, 2020

Related U.S. Application Data

(60) Provisional application No. 62/822,126, filed on Mar. 22, 2019.

(51) Int. Cl.
| | | |
|---|---|---|
| *A61K 9/00* | (2006.01) | |
| *A61K 31/135* | (2006.01) | |
| *A61K 31/138* | (2006.01) | |
| *A61K 47/10* | (2017.01) | |
| *A61M 15/00* | (2006.01) | |
| *A61M 15/08* | (2006.01) | |
| *A61K 47/14* | (2017.01) | |
| *A61K 47/20* | (2006.01) | |
| *A61K 47/36* | (2006.01) | |

(52) U.S. Cl.
CPC ............ *A61K 9/0043* (2013.01); *A61K 9/008* (2013.01); *A61K 31/135* (2013.01); *A61K 31/138* (2013.01); *A61K 47/10* (2013.01)

(58) Field of Classification Search
CPC ..... A61K 31/138; A61K 9/0043; A61K 9/008
See application file for complete search history.

(56) References Cited

U.S. PATENT DOCUMENTS

| | | | |
|---|---|---|---|
| 3,560,607 A | 2/1971 | Hartley | |
| 4,749,700 A * | 6/1988 | Wenig | A61K 31/44 514/249 |
| 5,756,537 A * | 5/1998 | Gill | A61K 31/337 514/451 |
| 5,989,535 A * | 11/1999 | Nayak | A61K 9/0031 424/430 |
| 6,399,610 B1 * | 6/2002 | Kurkela | A61K 31/50 514/249 |
| 8,911,751 B2 * | 12/2014 | Touitou | A61K 38/02 424/400 |
| 2004/0204399 A1 * | 10/2004 | Osbakken | A61P 31/04 514/217.05 |
| 2005/0069585 A1 * | 3/2005 | Kiel | A61K 31/205 424/464 |
| 2006/0120967 A1 * | 6/2006 | Namburi | A61K 36/00 424/45 |
| 2009/0312724 A1 * | 12/2009 | Pipkin | A61K 31/55 604/294 |
| 2016/0129205 A1 | 5/2016 | Shahaf et al. | |
| 2018/0000942 A1 | 1/2018 | Cunningham et al. | |
| 2018/0289639 A1 | 10/2018 | Potta et al. | |
| 2018/0344951 A1 | 12/2018 | Shahaf et al. | |
| 2022/0160656 A1 * | 5/2022 | Sramek | A61K 31/138 |

FOREIGN PATENT DOCUMENTS

| | | |
|---|---|---|
| CN | 1872168 A | 12/2006 |
| CN | 1965803 A | 5/2007 |
| JP | 4176859 B2 | 8/2008 |
| WO | 9746243 A1 | 12/1997 |

OTHER PUBLICATIONS

NPL search results provided by IP.com; downloaded May 12, 2020.*
Javed et al.; "Formulation Development and Evaluation of Diphenhydramine Nasal Nano-emulgel"; AAPS PharmSciTech, vol. 19, No. 4, pp. 1730-1742. Published May 2018.*
Santiago-Palma et al.; "Diphenhydramine as an Analgesic Adjuvant in Refractory Cancer Pain"; JPSM; vol. 22, No. 2, pp. 699-703. Published Aug. 2001.*
Chahal, Harinder; (Section 3: Antiallergics and Medicines Used in Anaphylaxis: Histamine-1 receptor antagonists—A critical evaluation to update Section 3; published online Jan. 9, 2016).*
Wayback Machine NPL download showing the online publication date of Jan. 9, 2016 for the Chahal reference. Downloaded Jan. 26, 2021.*
W. Steven Pray; "Insomnia and Its Treatment with Nonprescription Products"; US Pharmacist; 11-pg PDF; published on Apr. 20, 2009.*
Gaffey, et al., "Intranasally and Orally Administered Antihistamine Treatment of Experimental Rhinovirus Colds", American Review of Respiratory Disease, vol. 136:3, 1987, pp. 556-260.
Iwanaga, et al., "Usefulness of Liposomes as an Intranasal Dosage Formulation for Tropical Drug Application", Biol. Pharm. Bull., 2000, pp. 323-326.
International Search Report and Written Opinion issued in PCT/US2020/023539, dated Jun. 18, 2020.
Nandgude et al., Characterization of Hydrochloride and Tannate Salts of Diphenhydramine, Indian Journal of Pharmaceutical Sciences, vol. 70(4), pp. 482-486, 2008.

* cited by examiner

*Primary Examiner* — Jeffrey T. Palenik
(74) *Attorney, Agent, or Firm* — Meunier Carlin & Curfman LLC

(57) ABSTRACT

Disclosed herein are compositions including diphenhydramine, or a pharmaceutically acceptable salt thereof, and a liquid vehicle. The compositions may be administered intranasally to patients in need of diphenhydramine. The compositions provide increase plasma and brain concentrations relative to orally administered compositions, but without the limitations associated with intravenously administered compositions.

12 Claims, 6 Drawing Sheets

INTRANASALLY ADMINISTERED ANTIHISTAMINES AND USES THEREOF

CROSS-REFERENCE TO RELATED APPLICATION

This application claims the benefit of U.S. Provisional Application 62/822,126, filed on Mar. 22, 2019, the contents of which are hereby incorporated in its entirety.

FIELD OF THE INVENTION

The invention is directed to compositions for the intranasal administration of antihistamines, including diphenhydramine. The compositions provide rapid systemic absorption of diphenhydramine. The compositions may be used for a variety of purposes, including for the prevention and treatment of allergic rhinitis, urticaria, pruritus, or allergic reactions, managing pain, to treat vertigo or motion sickness, and as a sleep aid.

BACKGROUND

Diphenhydramine is an inverse agonist of the histamine Hi-receptor. Diphenhydramine can cross the blood brain barrier and agonizes Hi receptors centrally. Diphenhydramine is also a competitive antagonist of muscarinic acetylcholine receptors, and can block intracellular sodium channels. Because of this constellation of pharmacological activity, diphenhydramine has been used to treat conditions such as allergy, including allergic reactions, allergic reactions prior to anaphylaxis, common cold, motion sickness, insomnia, pain, and extrapyramidal symptoms such as dystonia, akathisia, parkinsonism, bradykinesia, tremor, and tardive dyskinesia.

Diphenhydramine is typically provided as the hydrochloride salt ("DPH"), and is available in orally administrable dosage forms, topically applied lotions, creams, sprays, and parenteral solutions for intravenous or intramuscular injection. Orally administered DPH reaches a peak plasma concentration two to three hours after administration. Due to this delay oral administration is not particularly suitable for emergent use of DPH, for instance to prevent anaphylaxis, or in other situations when rapid onset of DPH activity is desired, for instance as a sleep aid. Similarly, application of topical DPH to the skin does not result in meaningful systemic concentrations, and therefore suffers similar limitations as the oral form. Although intravenous administration of DPH results in essentially instantaneous peak plasma concentration, this route of administration should only be administered by a health care provider. Moreover, injection devices, when used improperly, can function as vectors for many different diseases, including HIV and hepatitis. Furthermore, even appropriate use of injection devices can cause adverse events, and generates potentially hazardous medical waste.

Nasal formulations have been recognized as a useful alternative to oral and parenteral administration. From a patient's perspective, nasal formulations are more convenient and less painful than parenteral administration. Nasal formulations also avoid hepatic first pass metabolism. However, in order to achieve systemic concentrations of an intranasally administered drug, the drug must be able to cross the mucosal membranes present in the nasal cavity. There are several different mechanisms by which drug uptake may be blocked after intranasal administration, including impermeability to cellular tissue as well as binding to mucin.

Simple aqueous nasal formulations of diphenhydramine have proved to be ineffective as an antihistamine treatment. Indeed, Gaffney asserts intranasal administration of diphenhydramine in a phosphate buffer vehicle, but observed no therapeutic effect in reducing the signs and symptoms associated with rhinovirus colds in patients. See Gaffney et al., "Intranasally and Orally Administered Antihistamine Treatment of Experimental Rhinovirus Colds," Amer. Rev. Respiratory Disease 136(3):556-560 (1987). Accordingly, there remains a need for improved, effective formulations of diphenhydramine that can be administered by lay persons. There remains a need for non-injectable diphenhydramine formulations that deliver rapid peak plasma concentrations of the drug.

SUMMARY

Disclosed herein are compositions of diphenhydramine, including diphenhydramine hydrochloride, for intranasal administration. The disclosed compositions represent a convenient alternative to parenteral injection of diphenhydramine.

The details of one or more embodiments are set forth in the descriptions below. Other features, objects, and advantages will be apparent from the description and from the claims.

DETAILED DESCRIPTION

Figure 1:
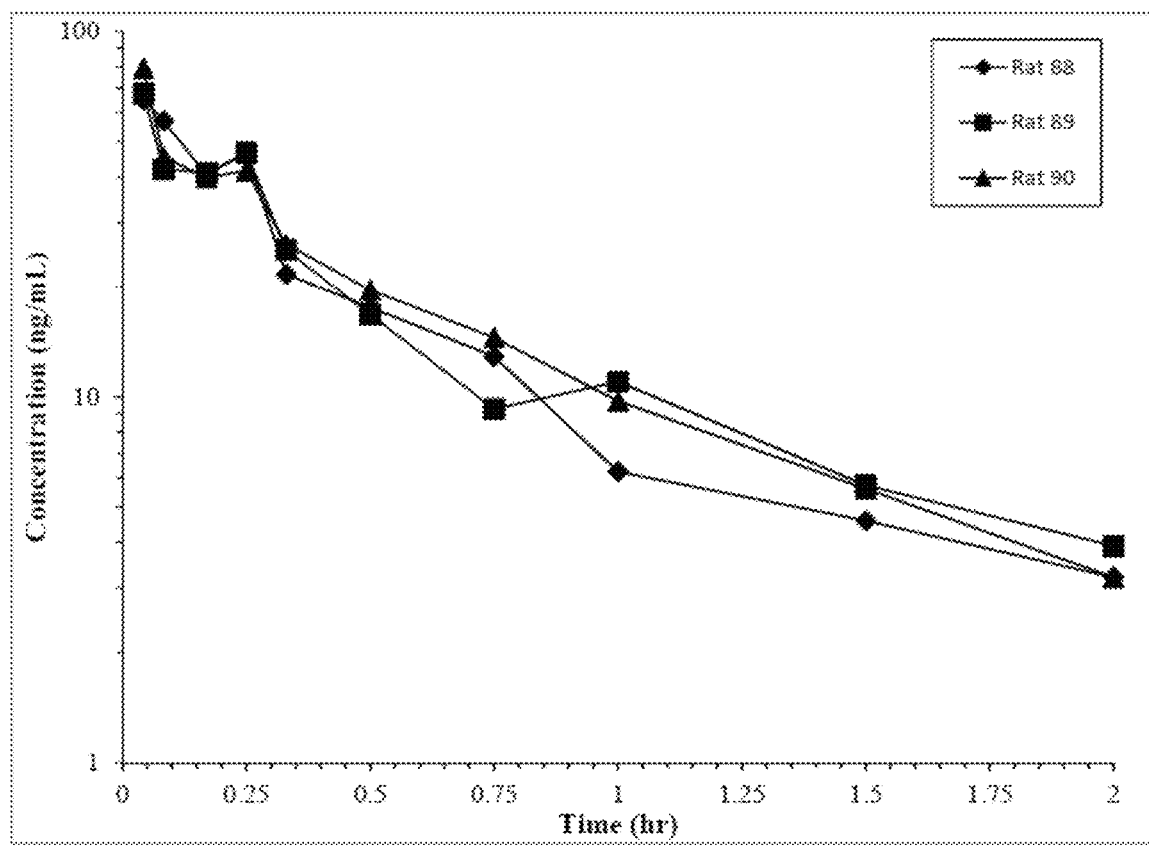
FIG. 1 depicts plasma concentrations arising after intravenous administration of diphenhydramine (0.357 mg/kg) to male Sprague-Dawley rats.

Before the present methods and systems are disclosed and described, it is to be understood that the methods and systems are not limited to specific synthetic methods, specific components, or to particular compositions. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein. It is understood that when combinations, subsets, interactions, groups, etc. of these components are disclosed, each of the various individual and collective combinations and permutations of these is specifically contemplated and described herein, for all methods and systems, even if not specifically referenced. This applies to all aspects of this application including, but not limited to, steps in disclosed methods. Thus, if there are a variety of additional steps that can be performed, it is understood that each of these additional steps can be performed with any specific embodiment or combination of embodiments of the disclosed methods.

Disclosed herein are compositions containing diphenhydramine, or a pharmaceutically acceptable salt thereof, that are intended for administration intranasally. In comparison with orally delivered diphenhydramine compositions, the compositions disclosed herein provide rapid systemic levels of diphenhydramine, comparable to intravenously administered diphenhydramine. In this context, the term "comparable" refers to a value having a magnitude that is up to three times larger than the magnitude of a reference value. In some embodiments, the compositions disclosed herein can provide a peak plasma concentration ($C_{max}$) of diphenhydramine of at least 5 nanograms per milliliter (ng/mL), at least 10 ng/mL, at least 20 ng/mL, at least 30 ng/mL, at least 40 ng/mL, at least 50 ng/mL, at least 60 ng/mL, at least 70 ng/mL, at least 80 ng/mL, at least 90 ng/mL, at least 100 ng/mL, at least 200 ng/mL, at least 300 ng/mL, at least 400 ng/mL, or at least 500 ng/mL. In some embodiments, the compositions disclosed herein can provide a peak plasma concentration ($C_{max}$) of diphenhydramine that is from 10-500 ng/mL, from 50-500 ng/mL, from 100-500 ng/mL, from 200-500 ng/mL, from 300-500 ng/mL, from 400-500 ng/mL, from 50-400 ng/mL, from 100-400 ng/mL, from 200-400 ng/mL, from 300-400 ng/mL, from 100-300 ng/mL, from 200-300 ng/mL, from 100-200 ng/mL, from 10-100 ng/mL, from 25-100 ng/mL, from 50-100 ng/mL, from 75-100 ng/mL, from 50-75 ng/mL, or from 25-50 ng/mL.

The time to reach peak plasma concentration ($T_{max}$) after administration of the compositions disclosed herein can be comparable to intravenously administered diphenhydramine. In this context, the term "comparable" refers to a value having a magnitude that is up to three times larger than the magnitude of a reference value. In some embodiments, nasal administration of the compositions disclosed herein provide a $T_{max}$ value of less than 10 minutes, less than 8 minutes, less than 6 minutes, less than 5 minutes, less than 4 minutes, less than 3 minutes, or less than 2 minutes. In some embodiments, nasal administration of the compositions disclosed herein provide a $T_{max}$ value that is from 1 minute to 10 minutes, from 1 minute to 8 minutes, from 1 minute to 6 minutes, from 1 minute to 5 minutes, from 1 minute to 4 minutes, from 1 minute to 3 minutes, or from 1 minute to 2 minutes. In some embodiments, nasal administration of the compositions disclosed herein provide a $T_{max}$ value of about 10 minutes, about 8 minutes, about 6 minutes, about 5 minutes, about 4 minutes, about 3 minutes, about 2 minutes, or about 1 minute.

In some embodiments, the compositions disclosed herein can be used to administer diphenhydramine directly to the brain and/or cerebrospinal fluid. The nasal system includes an olfactory bulb, which has nerve fibers leading to the temporal lobe of the cerebral cortex, along with the maxillary branch of the trigeminal nerves emanating from the nasal cavity. As these drug delivery mechanisms do not rely solely on the cardiovascular system, they can be used to provide therapeutic levels of diphenhydramine in the brain and/or cerebrospinal fluid comparable to those achieved following oral administration of the same dose. In this context, the term "comparable" refers to a value having a magnitude that is up to three times larger than the magnitude of a reference value. For example, diphenhydramine concentrations in amounts from 25-300 nanograms per gram (ng/g), from 50-300 ng/g, from 75-300 ng/g, from 100-300 ng/g, 150-300 ng/g, from 50-150 ng/g, from 75-150 ng/g, or from 100-150 ng/g can be obtained in brain tissue following intranasal administration of the disclosed compositions.

In an aspect, the diphenhydramine can access the brain and/or cerebrospinal fluids via an intracellular pathway, in which diphenhydramine is delivered via axonal transport to the olfactory bulb over the course of several hours. In an aspect, the diphenhydramine can be delivered to the olfactory bulb via an extracellular pathway, which likely proceeds via bulk flow transport through perineural channels. The extracellular delivery diphenhydramine permits rapid delivery (i.e., less than 10 minutes, less than 5 minutes, or less than 2 minutes) of the drug to the brain and/or cerebrospinal fluid. In one extracellular route, diphenhydramine crosses the gap between olfactory neurons in the olfactory epithelium and then delivered to the olfactory bulb.

Disclosed herein are compositions containing diphenhydramine, or a pharmaceutically acceptable salt thereof, in a liquid vehicle. In certain embodiments, the present disclosure is directed to diphenhydramine spray compositions comprising diphenhydramine, or a pharmaceutically acceptable salt thereof, and one or more excipients such as acids, solvents, antioxidants, preservatives, penetration enhancers, viscosity modifiers, sweeteners, sweetness enhancers, pH modifiers, isotonicity agents and flavoring agents.

Pharmaceutically acceptable salts are salts that retain the desired biological activity of the parent compound and do not impart undesirable toxicological effects. Examples of such salts are acid addition salts formed with inorganic acids, for example, hydrochloric, hydrobromic, sulfuric, phosphoric, and nitric acids and the like; salts formed with organic acids such as acetic, oxalic, tartaric, succinic, maleic, fumaric, gluconic, citric, malic, methanesulfonic, p-toluenesulfonic, napthalenesulfonic, and polygalacturonic acids, and the like. Pharmaceutically acceptable and non-pharmaceutically acceptable salts may be prepared using procedures well known in the art, for example, by reacting a sufficiently basic compound such as an amine with a suitable acid comprising a physiologically acceptable anion. In aspects, the disclosed compositions include diphenhydramine as a hydrochloride (1:1) salt or a citrate (1:1) salt. As used herein, reference to "diphenhydramine" includes both the free base and any pharmaceutically acceptable salts thereof. Reference to any particular mass of "diphenhydramine, or pharmaceutical salt thereof," refers to the mass equivalent of the free base. Reference to any particular mass of a specific salt of diphenhydramine, e.g., diphenhydramine hydrochloride, refers to the mass of the specific salt.

In some embodiments, the compositions comprise diphenhydramine or the pharmaceutically acceptable salt equivalent in an amount from 5%-50% of the weight of diphenhydramine per the weight of the composition (w/w), from 10%-50% w/w, from 15%-50% w/w, from 20%-50% w/w, from 20%-40% w/w, from 20%-30% w/w, from 5-10% w/w, from 7.5-12.5% w/w, from 1-7.5% w/w, from 1-5% w/w, or from 1-2.5% w/w.

In some embodiments, compositions comprise diphenhydramine or a pharmaceutically acceptable salt equivalent in an amount that is at least 1% w/w, at least 2.5% w/w, at least 5% w/w, at least 7.5% w/w, at least 10% w/w, at least 15% w/w, at least 20% w/w, at least 25% w/w, at least 30% w/w, at least 35% w/w, at least 40% w/w, at least 45% w/w, or at least 50% w/w.

In some embodiments, the compositions comprise diphenhydramine or a pharmaceutically acceptable salt equivalent in an amount that is about 1% w/w, about 2.5% w/w, about 5% w/w, about 7.5% w/w, about 10% w/w, about 15% w/w, about 20% w/w, about 25% w/w, about 30% w/w, about 35% w/w, about 40% w/w, about 45% w/w, or about 50% w/w.

In some embodiments, compositions comprise diphenhydramine hydrochloride in an amount from 5%-50% w/w, from 10%-50% w/w, from 15%-50% w/w, from 20%-50% w/w, from 20%-40% w/w, from 20%-30% w/w, from 5-15% w/w, from 10-15% w/w, from 1-10% w/w, from 2.5-10% w/w, from 5-10% w/w, from 7.5-12.5% w/w, from 1-7.5% w/w, from 1-5% w/w, or from 1-2.5% w/w.

In some embodiments, compositions comprise diphenhydramine hydrochloride in an amount that is at least 1% w/w, at least 2.5% w/w, at least 5% w/w, at least 7.5% w/w, at least 10% w/w, at least 15% w/w, at least 20% w/w, at least 25% w/w, at least 30% w/w, at least 35% w/w, at least 40% w/w, at least 45% w/w, or at least 50% w/w.

In some embodiments, compositions comprise diphenhydramine hydrochloride in an amount that is about 1% w/w, about 2.5% w/w, about 5% w/w, about 7.5% w/w, about 10% w/w, about 15% w/w, about 20% w/w, about 25% w/w, about 30% w/w, about 35% w/w, about 40% w/w, about 45% w/w, or about 50% w/w.

In some embodiments, diphenhydramine or a pharmaceutically acceptable salt equivalent is present in a liquid vehicle in a concentration that is from 5-500 mg/mL, from 50-500 mg/mL, from 100-500 mg/mL, from 250-500 mg/mL, from 100-400 mg/mL, from 200-400 mg/mL, from 300-400 mL, from 300-500 mg/mL, from 100-200 mg/mL, from 50-150 mg/mL, from 150-250 mg/mL, from 5-100 mg/mL, from 10-100 mg/mL, from 20-100 mg/mL, from 30-100 mg/mL, from 40-100 mg/mL, from 50-100 mg/mL, from 50-75 mg/mL, from 25-50 mg/mL, or from 25-75 mg/mL.

In some embodiments, diphenhydramine or a pharmaceutically acceptable salt equivalent is present in a liquid vehicle in a concentration that is at least 5 mg/mL, at least 10 mg/mL, at least 20 mg/mL, at least 30 mg/mL, at least 40 mg/mL, at least 50 mg/mL, at least 75 mg/mL, at least 100 mg/mL, at least 150 mg/mL, at least 200 mg/mL, at least 250 mg/mL, at least 300 mg/mL, at least 350 mg/mL, at least 400 mg/mL, at least 450 mg/mL, or at least 500 mg/mL.

In some embodiments, diphenhydramine or a pharmaceutically acceptable salt equivalent is present in a liquid vehicle in a concentration that is about 5 mg/mL, about 10 mg/mL, about 20 mg/mL, about 30 mg/ml, about 40 mg/mL, about 50 mg/mL, about 75 mg/mL, about 100 mg/mL, about 150 mg/mL, about 200 mg/mL, about 250 mg/mL, about 300 mg/mL, about 350 mg/mL, about 400 mg/mL, about 450 mg/mL, or about 500 mg/mL.

In some embodiments, diphenhydramine hydrochloride is present in a liquid vehicle in a concentration that is from 5-500 mg/mL, from 50-500 mg/mL, from 100-500 mg/mL, from 250-500 mg/mL, from 100-400 mg/mL, from 200-400 mg/mL, from 300-500 mg/mL, from 100-200 mg/mL, from 50-150 mg/mL, from 150-250 mg/mL, from 5-100 mg/mL, from 10-100 mg/mL, from 20-100 mg/mL, from 30-100 mg/mL, from 40-100 mg/mL, from 50-100 mg/mL, from 50-75 mg/mL, from 25-50 mg/mL, or from 25-75 mg/mL.

In some embodiments, diphenhydramine hydrochloride is present in a liquid vehicle in a concentration that is at least 5 mg/mL, at least 10 mg/mL, at least 20 mg/mL, at least 30 mg/mL, at least 40 mg/mL, at least 50 mg/mL, at least 75 mg/mL, at least 100 mg/mL, at least 150 mg/mL, at least 200 mg/mL, at least 250 mg/mL, at least 300 mg/mL, at least 350 mg/mL, at least 400 mg/mL, at least 450 mg/mL, or at least 500 mg/mL.

In some embodiments, diphenhydramine hydrochloride is present in a liquid vehicle in a concentration that is about 5 mg/mL, about 10 mg/mL, about 20 mg/mL, about 30 mg/mL, about 40 mg/mL, about 50 mg/mL, about 75 mg/mL, about 100 mg/mL, about 150 mg/mL, about 200 mg/mL, about 250 mg/mL, about 300 mg/mL, about 350 mg/mL, about 400 mg/mL, about 450 mg/mL, or about 500 mg/mL.

The liquid vehicle can comprise one or more solvents, including water, ethanol, glycerin, propylene glycol, and combinations thereof. In some embodiments, the liquid vehicle is water. In other embodiments, the liquid vehicle is a combination of water and at least one other solvent. In further embodiments, the at least one other solvent can be present in an amount from 0.5-50%, from 1-50%, from 1-30%, from 1-25%, from 1-20%, from 1-15%, from 1-10%, from 1-5%, from 5-30%, from 10-30%, from 15-30%, from 20-30%, from 10-20%, or from 5-10%, by weight, relative to the total weight of the liquid vehicle. In other further embodiments, the at least one other solvent can be present in an amount that is at least 0.5%, at least 1%, at least 2.5%, at least 5%, at least 10%, at least 15%, at least 20%, at least 25%, or at least 30% by weight, relative to the total weight of the liquid vehicle. In yet other further embodiments, the at least one other solvent can be present in an amount that is at 0.5%, 1%, 2.5%, 5%, 10%, 15%, 20%, 25%, or 30% by weight, relative to the total weight of the liquid vehicle.

In some embodiments, solvent combinations are a mixture of propylene glycol and water, as well as a mixture of glycerin and water. In some embodiments, the compositions disclosed herein include a polyethylene glycol having a molecular weight that is less than 2,500 Daltons (Da), less than 2,000 Da, less than 1,500 Da, less than 1,000 Da, less than 750 Da, less than 500 Da, less than 400 Da, or less than 300 Da. In some embodiments, polyethylene glycol is present in the liquid vehicle in an amount from 0.5-50%, from 1-50%, from 1-30%, from 1-25%, from 1-20%, from 1-15%, from 1-10%, from 1-5%, from 5-30%, from 10-30%, from 15-30%, from 20-30%, from 10-20%, or from 5-10%, by weight, relative to the total weight of the liquid vehicle. In some embodiments, polyethylene glycol is present in the liquid vehicle in an amount that is at least 0.5%, at least 1%, at least 5%, at least 10%, at least 15%, at least 20%, at least 25%, or at least 30% by weight, relative to the total weight of the liquid vehicle. In some embodiments, polyethylene glycol is present in the liquid vehicle in an amount that is 0.5%, 1%, 5%, 10%, 15%, 20%, 25%, or 30% by weight, relative to the total weight of the liquid vehicle.

In some embodiments, compositions do not include any propellant (e.g., a fluorocarbon, chlorofluorocarbon, or hydrocarbon propellant). In some embodiments, compositions include a propellant. In aspects, the compositions of the present disclosure do not include liposomes. In aspects, the intranasal delivery system of the present disclosure is not liposome-based.

In an aspect, the diphenhydramine spray comprises at least one antioxidant. Exemplary antioxidants include butylated hydroxyanisole (BHA), butylated hydroxytoluene (BHT), ascorbic acid, methionine, sodium ascorbate, sodium thiosulfate, sodium bisulfite, sodium metabisulfite, ascorbyl palmitate, thioglycerol, alpha tocopherol (vitamin E), cysteine hydrochloride, citric acid, sodium citrate, and combinations thereof. In some embodiments, the antioxidant can be present at a concentration from 0.005%-5%, from 0.005%-2.5%, from 0.005%-1%, from 0.005%-0.5%, from 0.05%-0.5%, from 0.05%-1%, from 0.1-1%, from 0.5-2.5%, or from 1-2% by weight, relative to the total weight of the composition. In some embodiments, the antioxidant can be present at a concentration of at least 0.005%, at least 0.01%, at least 0.05%, at least 0.1%, at least 0.5%, at least 1%, at least 1.5%, at least 2%, at least 2.5%, at least 3%, at least 4%, or at least 5% by weight, relative to the total weight of the composition. In some embodiments, the antioxidant can be present at a concentration of about 0.005%, about 0.01%, about 0.05%, about 0.1%, about 0.5%, about 1%, about 1.5%, about 2%, about 2.5%, about 3%, about 4%, or about 5% by weight, relative to the total weight of the composition.

In an aspect, the diphenhydramine spray includes at least one preservative. Exemplary preservatives include benzoyl alcohol, phenyl ethyl alcohol, butyl paraben, methyl paraben, ethyl paraben, propyl paraben, sodium benzoate, chlorobutanol, thioglycerol, benzalkonium chloride, citric acid, ethylenediaminetetraacetic acid (EDTA), sodium citrate, propyl gallate, 8-hydroxyquinoline, boric acid, histidine, and combinations thereof. The preservative can be present at a concentration from 0.005%-5%, from 0.005%-2.5%, from 0.005%-1%, from 0.005%-0.5%, from 0.05%-0.5%, from 0.05%-1%, from 0.1-1%, from 0.5-2.5%, or from 1-2% by weight, relative to the total weight of the composition. In some embodiments, the preservative can be present at a concentration of at least 0.005%, at least 0.01%, at least 0.05%, at least 0.1%, at least 0.5%, at least 1%, at least 1.5%, at least 2%, at least 2.5%, at least 3%, at least 4%, or at least 5% by weight, relative to the total weight of the composition. In some embodiments, the preservative can be present at a concentration of about 0.005%, about 0.01%, about 0.05%, about 0.1%, about 0.5%, about 1%, about 1.5%, about 2%, about 2.5%, about 3%, about 4%, or about 5% by weight, relative to the total weight of the composition.

In an aspect, the diphenhydramine spray compositions of the present disclosure can include at least one penetration enhancer. Suitable classes of penetration enhancers include fatty acids, positively charged polymers such as oligosaccharides, anionic surfactants, cationic surfactants, and the like. Exemplary penetration enhancers include menthol, limonene, carvone, methyl chitosan, chitosan oligosaccharides, polysorbates, saponins, polyoxyethylene-9-lauryl ether, sodium lauryl sulfate, glyceryl oleate, dipalmitoyl phosphatidyl choline, soybean lecithin, phosphatidylcholine, caproic acid, enanthic acid, pelargonic acid, capric acid, undecylenic acid, lauric acid, myristic acid, palmitic acid, oleic acid, stearic acid, linolenic acid, arachidonic acid, benzethonium chloride, benzethonium bromide, benzalkonium chloride (BKC), cetylpyridium chloride, edetate disodium dihydrate, sodium desoxycholate, sodium deoxyglycolate, sodium glycocholate, sodium taurocholate, sodium deoxycholate sodium, glycodeoxycholate, sodium caprate, sodium taurocholate, sodium hydroxybenzoyal amino caprylate, dodecyl dimethyl aminopropionate, L-lysine, glycerol oleate, glyceryl monostearate, citric acid, peppermint oil, cyclodextrins, methylated cyclodextrins, chitosan, caprylic acid, and salts of caprylic acid. Preferred penetration enhancers include sodium lauryl sulfate, chitosan oligosaccharides, and sodium caprylate.

In some embodiments, the at least one penetration enhancer can be present in the composition at a concentration from 0.1-10% w/w, from 0.1-5% w/w, from 0.1-2.5% w/w, from 1-10% w/w, from 1-5% w/w, from 1-2.5% w/w, from 2.5-10% w/w, or from 5-10% w/w. In some embodiments, the at least one penetration enhancer can be present in the composition at a concentration of at least 0.1% w/w, at least 0.5% w/w, at least 1% w/w, at least 1.5% w/w, at least 2% w/w, at least 2.5% w/w, at least 5% w/w, or at least 10% w/w. In some embodiments, the at least one penetration enhancer can be present in the composition at a concentration of about 0.1% w/w, about 0.5% w/w, about 1% w/w, about 1.5% w/w, about 2% w/w, about 2.5% w/w, about 5% w/w, or about 10% w/w. In some embodiments of the present disclosure, the diphenhydramine spray compositions do not include any penetration enhancer.

In an aspect, the diphenhydramine spray compositions of the present disclosure comprise at least one viscosity modifier. Viscosity modifiers suitable for the present disclosure include, but are not limited to, polyvinylpyrrolidone, carboxymethyl cellulose, hydroxypropyl methyl cellulose ("HPMC"), methyl cellulose, hydroxyethyl cellulose, glycerin, polyvinyl alcohol and combinations thereof. In an embodiment, the viscosity modifier is HPMC. In some embodiments, the viscosity modifier is present in the composition in an amount from 0.1-5%, from 0.1-0.5%, from 0.5-1%, from 1-2%, from 2-3%, from 3-4%, or from 4-5% by weight, relative to the total weight of the composition. In some embodiments, the viscosity modifier is present in the composition in an amount of at least 0.1%, at least 0.5%, at least 1%, at least 1.5%, at least 2%, at least 2.5%, at least 3%, at least 4%, or at least 5% by weight, relative to the total weight of the composition. In some embodiments, the viscosity modifier is present in the composition in an amount of about 0.1%, about 0.5%, about 1%, about 1.5%, about 2%, about 2.5%, about 3%, about 4%, or about 5% by weight, relative to the total weight of the composition.

The dynamic viscosity of the spray composition, measured at room temperature (23° C.), can be at least 5 centipoise (cP), at least 10 cP, or at least 35 cP. In some embodiments, the dynamic viscosity can be between 5 and 100 cP, between 25 and 100 cP, between 50 and 100 cP, between 75 and 100 cP, between 5 and 50 cP, between 10 and 50 cP, between 15 and 50 cP, or between 25 and 50 cP, In an aspect, the diphenhydramine spray compositions of the present disclosure include at least one isotonicity agent. Exemplary isotonicity agents include sodium chloride, dextrose, glycerin, sucrose, urea, propylene glycol, boric acid, phenobarbital, zinc sulfate, magnesium sulfate, sodium sulfate, zinc chloride, calcium bromide, sodium phosphate, sodium citrate, sodium borate, and potassium borate. In some embodiments, the isotonicity agent is present in the composition in an amount from 0.1-5%, from 0.1-0.5%, from 0.5-1%, from 1-2%, from 2-3%, from 3-4%, or from 4-5% by weight, relative to the total weight of the composition. In some embodiments, the isotonicity agent is present in the composition in an amount of at least 0.1%, at least 0.5%, at least 1%, at least 1.5%, at least 2%, at least 2.5%, at least 3%, at least 4%, or at least 5% by weight, relative to the total weight of the composition. In some embodiments, the isotonicity agent is present in the composition in an amount of about 0.1%, about 0.5%, about 1%, about 1.5%, about 2%, about 2.5%, about 3%, about 4%, or about 5% by weight, relative to the total weight of the composition.

In an aspect, the diphenhydramine spray compositions of the present disclosure include at least one sweetener. Sweeteners suitable for the present disclosure include, but are not limited to, sucralose, sucrose, aspartame, saccharin, dextrose, mannitol, glycerin, xylitol and combinations thereof. In an embodiment, the sweetener is sucralose. In an aspect, the diphenhydramine spray he compositions include a sweetness enhancer. Sweetness enhancers suitable for the present disclosure include, but are not limited to, the ammonium salt forms of crude and refined Glycyrrhizic Acid. Magnasweet® products (available from Mafco Worldwide Corporation, Magnasweet is a registered trademark of Mafco Worldwide Corporation) use the ammonium salt forms of crude and refined Glycyrrhizic Acid. Glycyrrhizic Acid is also available as a pure derivative in the sodium and potassium salt forms. In some embodiments, a sweetness enhancer is present in the composition in an amount of about 0.001% to about 1% by weight, relative to the total weight of the composition.

The diphenhydramine spray compositions of the present disclosure can be formulated with a variety of pH ranges. For example, the compositions can have a pH from 2.0-8.0, from 3.0-7.0, from 3.0-6.5, from 3.5-6.5, from 4.5-6.5, from 5.0-6.5, from 5.5-6.5, from 6.0-6.5, from 3.0-6.0, from 3.0-6.0, from 3.5-6.0, from 4.5-6.0, from 5.0-6.0, from 5.5-6.0, from 3.0-5.5, from 3.5-5.5, from 4.0-5.5, from 4.5-5.5, or from 5.0-5.5. In an embodiment, the compositions of the present disclosure are at a pH from about 5.0 to about 6.0. The pH can be controlled by inclusion of the appropriate amount of a suitable acid or base, such as hydrochloric acid, citric acid, fumaric acid, lactic acid, malic acid, tartaric acid, succinic acid, sodium hydroxide, sodium citrate, sodium bicarbonate, sodium carbonate, ammonium carbonate and combinations thereof.

The compositions disclosed herein may be intranasally administered to a patient in need thereof using a suitable spray device. Nasal spray devices known in the art, such as a needle-free device or a "ready-to-use" device, wherein minimal or no manipulations are required to use the device and administer the composition into a nostril. The nasal spray device, in some aspects, may be a disposable device suitable for placement in household trash and not requiring formal hazardous waste disposal as is true for needle-based delivery. The device can comprise a reservoir and means for expelling the pharmaceutical dose in the form of a spray, where a quantity of the pharmaceutical composition is contained within the reservoir. In an embodiment, the device, which can be suitable for expelling a single or multiple doses, can include a metering pump, which can be finger or hand-actuated. It may be designed to administer the intended dose with multiple sprays, e.g., two sprays, e.g., one spray in each nostril, or as a single spray, e.g., in one nostril, or to vary the dose in accordance with the body weight or maturity of the patient.

In aspects, the spray device administers a volume of liquid from about 25-500 μL, from about 50-500 μL, from about 100-500 μL, from about 200-500 μL, from about 300-500 μL, from about 400-500 μL, from about 25-400 μL, from about 50-400 μL, from about 100-400 μL, from about 200-400 μL, from about 300-400 μL, from about 25-300 μL, from about 50-300 μL, from about 100-300 μL, from about 200-300 μL, from about 25-200 μL, from about 50-200 μL, from about 100-200 μL, from about 25-100 μL, from about 50-100 μL, or from about 25-50 μL.

In some aspects, the spray device administers a volume of liquid of at least 25 μL, at least 50 μL, at least 100 μL, at least 150 μL, at least 200 μL, at least 250 μL, at least 300 μL, at least 400 μL, at least 500 μL, or at least 750 μL. In some aspects, the spray device administers a volume of liquid that is about 25 μL, about 50 μL, about 100 μL, about 150 μL, about 200 μL, about 250 μL, about 300 μL, about 400 μL, about 500 μL, or about 750 μL.

In some embodiments, the volumes described above are delivered to a single nostril, while in other embodiments, the volumes described above are delivered in approximately equal amounts to each nostril.

The compositions disclosed herein are capable of producing a variety of different droplet size distributions. Droplet size can be characterized by a volume mean diameter ($D_{v50}$), where half of the volume of droplets in the spray are smaller than the average (mean) droplet size, and half of the volume of droplets in the spray are larger than the average droplet size. Similarly, a mean $D_{v10}$ value, where 10% of the volume of droplets in the spray are smaller than the average droplet size, and a $D_{v90}$ value, where 90% of the volume of droplets in the spray are smaller than the average droplet size, can also be determined.

In some embodiments, the diphenhydramine spray compositions of the present disclosure are characterized by a droplet size distribution having a $D_{v10}$ value is between 1-50 μm, between 5-50 μm, between 5-40 μm, between 5-25 μm, between 10-25 μm, or between 15-25 μm, as measured at a 3 cm distance from the dispensing nozzle during administration. In some embodiments, the diphenhydramine spray compositions of the present disclosure are characterized by a droplet size distribution having a $D_{v50}$ value is between 10-150 μm, between 10-100 μm, between 10-75 μm, between 10-50 μm, between 25-50 μm, or between 25-40 μm, as measured at a 3 cm distance from the dispensing nozzle during administration. In some embodiments, the diphenhydramine spray compositions of the present disclosure are characterized by a droplet size distribution wherein the $D_{v90}$ value is between 50-500 μm, from 50-300 μm, or from 100-300 μm, as measured at a 3 cm distance from the dispensing nozzle during administration.

The compositions disclosed herein can also be characterized by their spray patterns. One method for assessing a spray pattern is by calculating the relative spray span, which is determined by subtracting the $D_{v10}$ value from the $D_{v90}$ value and dividing by the $D_{v50}$ value. In some embodiments, the diphenhydramine spray compositions of the present disclosure are characterized by a relative spray span (($D_{v90}$−$D_{v10}$)/$D_{v50})$ that is between 1-15, between 1-10, between 2-10, between 2-8, or between 3-7, as measured at a 3 cm distance from the dispensing nozzle during administration.

In some aspects, methods for characterizing a spray pattern is by determining $D_{min}$, $D_{max}$, and ovality values, where the ovality of a spray pattern is calculated to be the ratio of $D_{max}$ to $D_{min}$. In some embodiments, the diphenhydramine spray compositions of the present disclosure are characterized by a spray pattern having a $D_{min}$ value that is between 5-50 mm, between 5-40 mm, between 5-30 mm, between 5-25 mm, between 5-20 mm, between 5-15 mm, between 10-50, between 10-40 mm, between 10-30 mm, between 10-25 mm, between 10-20 mm, between 10-15 mm, between 15-50, between 15-40 mm, between 15-30 mm, between 15-25 mm, between 15-20 mm, between 20-50, between 20-40 mm, between 20-30 mm, or between 20-25 mm, as measured at a 3 cm distance from the dispensing nozzle during administration. In some embodiments, the diphenhydramine spray compositions of the present disclosure are characterized by a spray pattern having a $D_{max}$ value that is between 15-100 mm, between 25-100, between 25-75 mm, or between 25-50 mm, as measured at a 3 cm distance from the dispensing nozzle during administration. In some embodiments, the diphenhydramine spray compositions of the present disclosure are characterized by a spray pattern having an ovality value that is between 1.0-2.0, between 1.25-2.0, between 1.25-1.75, between 1.25-1.50, between 1.5-2.0, or between 1.5-1.75, as measured at a 3 cm distance from the dispensing nozzle during administration.

The compositions disclosed herein are capable of producing a variety of different plume geometries. Plume geometry can be characterized by plume width, which is the width of the spray plume at a fixed distance from the spray nozzle. Alternatively, plume geometry can be characterized by spray angle, or the angle of the emitted plume measured from the vertex of the spray cone and spray nozzle to a fixed distance from the spray nozzle. In some embodiments, the diphenhydramine spray compositions of the present disclosure are characterized by a spray angle that is between 25°-75°, between 35°-75°, between 45°-75°, between 25°-50°, or between 35°-50°, at a 3 cm distance from the dispensing nozzle during administration. In some embodiments, the compositions are characterized by a plume width that is between 10-75 mm, between 10-50 mm, between 25-50 mm, or between 25-40 mm, at a 3 cm distance from the dispensing nozzle during administration.

The compositions disclosed herein may be used to treat any condition for which diphenhydramine may be used. The compositions may be administered to a patient in order to abort or reduce the severity of an allergic reaction, including an anaphylactic reaction, for instance occurring after an animal (insect, spider, etc.) bite or food allergy. The compositions may be administered to a patient to treat colds, viruses, and seasonal allergies like hay fever. The compositions may be administered to a patient to reduce or prevent migraine. The compositions may be administered to reduce or prevent motion sickness, including symptoms of motion sickness like nausea, vomiting, and dizziness. The compositions may be administered to a patient to treat nausea and/or vomiting that is not associated with motion sickness, for instance nausea and/or vomiting associated with a migraine. The compositions may be administered to treat insomnia, including short-term treatment of insomnia characterized by difficulties with sleep initiation. The compositions may be administered to a patient to treat or reduce extrapyramidal symptoms associated with neurological disorders such as Parkinson's disease, or drug-induced Parkinsonian symptoms such as akathisia, dystonic reaction, and bradykinesia. The compositions may be administered to a patient to treat or reduce cough.

The compositions may also be used to treat pain. In some embodiments, the compositions may be used to treat acute pain, chronic pain, breakthrough pain, bone pain, soft tissue pain, nerve pain, referred pain, and phantom pain. The pain may be the result of a variety of different pathophysiologies, for instance chronic back pain, spinal cord injuries, peripheral nerve injuries, traumatic brain injuries, neurodegenerative disorders, fibromyalgia, postherpetic neuralgia, diabetic neuropathy, traumatic mononeuropathy, complex regional pain syndrome, rhizotomy/nerve ablation, chemical exposure, chemotherapy-induced neuropathy, cancer, opioid withdrawal, and chronic neuropathic pain. In some embodiments, the compositions may be co-administered with a second agent, for example opioids and opioid peptides, morphine, hydroxymorphine, fentanyl, oxycodone, codeine, capsaicin, antiepileptic drugs (e.g., carbamazepine, primidone, gabapentin, pregabalin, diazepam, felbamate, fluorofelbamate, lamotrigine, lacosamide, levetiracetam, phenobarbital, phenyloin, fos-phenyloin, topiramate, valproate, vigabatrin, zonisamide, and oxcarbazepine), nonsteroidal anti-inflammatory drugs (NSAIDs), local anesthetics (e.g., lidocaine), glutamate receptor antagonists, NMDA antagonists, alpha-adrenoceptor agonists and antagonists, adenosine, cannabinoids, NK-1 antagonists (e.g., CI-021), antidepressants (e.g., amitriptyline, desipramine, imipramine), analogs and derivatives of galanin, somatostatin, neurotensin, neuropeptide Y, delta-sleep inducing peptide, enkephalins, oxytocin, cholecystikinin, calcitonin, cortistatin, nociceptin and other neuropeptide-based therapeutics.

In some embodiments, intranasal administration of a pharmaceutical composition comprising diphenhydramine or a pharmaceutically acceptable salt thereof used to treat insomnia provides a peak plasma concentration ($C_{max}$) of diphenhydramine that is at least 15 ng/mL, at least 20 ng/mL, at least 30 ng/mL, at least 40 ng/mL, at least 50 ng/mL, at least 60 ng/mL, at least 70 ng/mL, at least 80 ng/mL, at least 90 ng/mL, at least 100 ng/mL, at least 200 ng/mL, at least 300 ng/mL, at least 400 ng/mL, or at least 500 ng/mL.

In some embodiments, intranasal administration of a pharmaceutical composition comprising diphenhydramine or a pharmaceutically acceptable salt thereof used to treat insomnia provides a peak plasma concentration ($C_{max}$) of diphenhydramine that is from 15-500 ng/mL, from 25-500 ng/mL, from 50-500 ng/mL, from 100-500 ng/mL, from 200-500 ng/mL, from 300-500 ng/mL, from 400-500 ng/mL, from 15-400 ng/mL, from 25-400 ng/mL, from 50-400 ng/mL, from 100-400 ng/mL, from 200-400 ng/mL, from 300-400 ng/mL, from 15-300 ng/mL, from 25-300 ng/mL, from 50-300 ng/mL, from 100-300 ng/mL, from 200-300 ng/mL, from 15-200 ng/mL, from 25-200 ng/mL, from 50-200 ng/mL, from 100-200 ng/mL, from 15-100 ng/mL, from 25-100 ng/mL, from 50-100 ng/mL, from 75-100 ng/mL, from 15-75 ng/mL, from 25-75 ng/mL, from 50-75 ng/mL, from 15-50 ng/mL, from 25-50 ng/mL, or from 15-25 ng/mL.

In some embodiments, intranasal administration of a pharmaceutical composition comprising diphenhydramine or a pharmaceutically acceptable salt thereof used to treat insomnia provides a peak plasma concentration ($C_{max}$) of diphenhydramine that is about 15 ng/mL, about 20 ng/mL, about 30 ng/mL, about 40 ng/mL, about 50 ng/mL, about 60 ng/mL, about 70 ng/mL, about 80 ng/mL, about 90 ng/mL, about 100 ng/mL, about 200 ng/mL, about 300 ng/mL, about 400 ng/mL, or about 500 ng/mL.

In some embodiments, intranasal administration of a pharmaceutical composition comprising diphenhydramine or a pharmaceutically acceptable salt thereof used to treat an allergic reaction in children provides a peak plasma concentration ($C_{max}$) of diphenhydramine that is at least 15 ng/mL, at least 20 ng/mL, at least 25 ng/mL, at least 30 ng/mL, at least 40 ng/mL, at least 45 ng/mL, at least 50 ng/mL, at least 55 ng/mL, at least 60 ng/mL, at least 70 ng/mL, at least 80 ng/mL, at least 90 ng/mL, at least 100 ng/mL, at least 200 ng/mL, at least 300 ng/mL, at least 400 ng/mL, or at least 500 ng/mL.

In some embodiments, intranasal administration of a pharmaceutical composition comprising diphenhydramine or a pharmaceutically acceptable salt thereof used to treat an allergic reaction in children provides a peak plasma concentration ($C_{max}$) of diphenhydramine that is from 15-500 ng/mL, 30-500 ng/mL, from 50-500 ng/mL, from 100-500 ng/mL, from 200-500 ng/mL, from 300-500 ng/mL, from 400-500 ng/mL, from 15-400 ng/mL, from 30-400 ng/mL, from 50-400 ng/mL, from 100-400 ng/mL, from 200-400 ng/mL, from 300-400 ng/mL, from 15-300 ng/mL, from 30-300 ng/mL, from 50-300 ng/mL, from 100-300 ng/mL, from 200-300 ng/mL, from 15-200 ng/mL, from 30-200 ng/mL, from 50-200 ng/mL, from 100-200 ng/mL, from 15-100 ng/mL, from 30-100 ng/mL, from 40-100 ng/mL, from 50-100 ng/mL, from 60-100 ng/mL, from 75-100 ng/mL, from 15-75 ng/mL, from 30-75 ng/mL, from 40-75 ng/mL, from 45-75 ng/mL, from 50-75 ng/mL, from 55-75 ng/mL, from 60-75 ng/mL, from 15-60 ng/mL, from 30-60 ng/mL, from 40-60 ng/mL, from 45-60 ng/mL, from 50-60 ng/mL, from 55-60 ng/mL, from 15-50 ng/mL, from 30-50 ng/mL, from 40-50 ng/mL, from 45-50 ng/mL, from 30-45 ng/mL, from 40-45 ng/mL, from 30-40 ng/mL, or from 15-30 ng/mL.

In some embodiments, intranasal administration of a pharmaceutical composition comprising diphenhydramine or a pharmaceutically acceptable salt thereof used to treat an allergic reaction in children provides a peak plasma concentration ($C_{max}$) of diphenhydramine that is about 15 ng/mL, about 20 ng/mL, about 25 ng/mL, about 30 ng/mL, about 40 ng/mL, about 45 ng/mL, about 50 ng/mL, about 55 ng/mL, about 60 ng/mL, about 70 ng/mL, about 80 ng/mL, about 90 ng/mL, about 100 ng/mL, about 200 ng/mL, about 300 ng/mL, about 400 ng/mL, or about 500 ng/mL.

In some embodiments, intranasal administration of a pharmaceutical composition comprising diphenhydramine or a pharmaceutically acceptable salt thereof used to treat an allergic reaction in adults provides a peak plasma concentration ($C_{max}$) of diphenhydramine that is at least 30 ng/mL, at least 40 ng/mL, at least 50 ng/mL, at least 60 ng/mL, at least 70 ng/mL, at least 80 ng/mL, at least 90 ng/mL, at least 95 ng/mL, at least 100 ng/mL, at least 105 ng/mL, at least 110 ng/mL, at least 120 ng/mL, at least 130 ng/mL, at least 150 ng/mL, at least 200 ng/mL, at least 300 ng/mL, at least 400 ng/mL, or at least 500 ng/mL.

In some embodiments, intranasal administration of a pharmaceutical composition comprising diphenhydramine or a pharmaceutically acceptable salt thereof used to treat an allergic reaction in adults provides a peak plasma concentration ($C_{max}$) of diphenhydramine that is from 30-500 ng/mL, from 50-500 ng/mL, from 70-500 ng/mL, from 80-500 ng/mL, from 90-500 ng/mL, from 100-500 ng/mL, from 150-500 ng/mL, from 200-500 ng/mL, from 300-500 ng/mL, from 400-500 ng/mL, from 30-400 ng/mL, from 50-400 ng/mL, from 70-400 ng/mL, from 80-400 ng/mL, from 90-400 ng/mL, from 100-400 ng/mL, from 150-400 ng/mL, from 300-400 ng/mL, from 300-400 ng/mL, from 30-300 ng/mL, from 50-300 ng/mL, from 70-300 ng/mL, from 80-300 ng/mL, from 90-300 ng/mL, from 100-300 ng/mL, from 150-300 ng/mL, from 200-300 ng/mL, from 30-200 ng/mL, from 50-200 ng/mL, from 70-200 ng/mL, from 80-200 ng/mL, from 90-200 ng/mL, from 100-200 ng/mL, from 150-200 ng/mL, from 30-150 ng/mL, from 50-150 ng/mL, from 70-150 ng/mL, from 80-150 ng/mL, from 90-150 ng/mL, from 100-150 ng/mL, from 80-110 ng/mL, from 30-100 ng/mL, from 50-100 ng/mL, from 70-100 ng/mL, from 80-100 ng/mL, from 90-100 ng/mL, from 85-95 ng/mL, from 30-90 ng/mL, from 50-90 ng/mL, from 70-90 ng/mL, from 80-90 ng/mL, from 30-80 ng/mL, from 50-80 ng/mL, from 70-80 ng/mL, from 30-70 ng/mL, from 50-70 ng/mL, or from 30-50 ng/mL.

In some embodiments, intranasal administration of a pharmaceutical composition comprising diphenhydramine or a pharmaceutically acceptable salt thereof used to treat an allergic reaction in adults provides a peak plasma concentration ($C_{max}$) of diphenhydramine that is about 30 ng/mL, about 40 ng/mL, about 50 ng/mL, about 60 ng/mL, about 70 ng/mL, about 80 ng/mL, about 90 ng/mL, about 95 ng/mL, about 100 ng/mL, about 105 ng/mL, about 110 ng/mL, about 120 ng/mL, about 130 ng/mL, about 150 ng/mL, about 200 ng/mL, about 300 ng/mL, about 400 ng/mL, or about 500 ng/mL.

As used herein, the term patient refers to humans and non-human mammals, e.g., dogs, cats, horses, cows, etc. In some embodiments, the patient is a human. In some embodiments, the compositions disclosed herein may be used to administer diphenhydramine to pediatric patients, including infants. In some embodiments, the patient is from 1-5 years old. In some embodiments, the patient is less than 1 year old.

Various embodiments of the disclosed formulations are described below in Tables 1-8, where AA=antioxidant; Pres.=preservative; PE=penetration enhancer(s); VM=viscosity modifier; IA=isotonicity agent; solv.=non-water solvent; $PEG^A$=a first polyethylene glycol having a MW that is between 300-1,500; $PEG^B$=a second polyethylene glycol having a MW that is between 300-1,500; PPG=propylene glycol; Gly.=glycerin; $PE^A$=sodium caprylate; $PE^B$=chitosan oligosaccharide; $PE^C$=sodium lauryl sulfate; $PE^D$=β-cyclodextrin. For all of the formulations disclosed in Tables 1-8, water is the liquid vehicle.

TABLE 1

Compositions of Formulations 1a-4d

| | Formulation Number | | | |
|---|---|---|---|---|
| | 1 | 2 | 3 | 4 |
| DPH (mg/ml) | a) 25-75<br>b) 75-125<br>c) 125-250<br>d) 250-500 | a) 25-75<br>b) 75-125<br>c) 125-250<br>d) 250-500 | a) 25-75<br>b) 75-125<br>c) 125-250<br>d) 250-500 | a) 25-75<br>b) 75-125<br>c) 125-250<br>d) 250-500 |
| $PEG^A$ (w/w) | 1-10% | 10-15% | 15-20% | 20-30% |
| $PEG^B$ (w/w) | 0% | 0% | 0% | 0% |
| AA (w/w) | 0.1-1% | 0.1-1% | 0.1-1% | 0.1-1% |
| Pres. (w/w) | 0.1-1% | 0.1-1% | 0.1-1% | 0.1-1% |
| PE (w/w) | 0-5% | 0-5% | 0-5% | 0-5% |
| VM (w/w) | 0-5% | 0-5% | 0-5% | 0-5% |
| IA (w/w) | 0-5% | 0-5% | 0-5% | 0-5% |
| pH range | 3-6 | 3-6 | 3-6 | 3-6 |

TABLE 2

Compositions of Formulations 5a-8d

| | Formulation Number | | | |
|---|---|---|---|---|
| | 5 | 6 | 7 | 8 |
| DPH (mg/ml) | a) 25-75<br>b) 75-125<br>c) 125-250<br>d) 250-500 | a) 25-75<br>b) 75-125<br>c) 125-250<br>d) 250-500 | a) 25-75<br>b) 75-125<br>c) 125-250<br>d) 250-500 | a) 25-75<br>b) 75-125<br>c) 125-250<br>d) 250-500 |
| $PEG^A$ (w/w) | 0% | 0% | 0% | 0% |
| $PEG^B$ (w/w) | 1-10% | 10-15% | 15-20% | 20-30% |
| AA (w/w) | 0.1-1% | 0.1-1% | 0.1-1% | 0.1-1% |
| Pres. (w/w) | 0.1-1% | 0.1-1% | 0.1-1% | 0.1-1% |
| PE (w/w) | 0-5% | 0-5% | 0-5% | 0-5% |
| VM (w/w) | 0-5% | 0-5% | 0-5% | 0-5% |
| IA (w/w) | 0-5% | 0-5% | 0-5% | 0-5% |
| pH range | 3-6 | 3-6 | 3-6 | 3-6 |

TABLE 3

Compositions of Formulations 9a-12d

| | Formulation Number | | | |
|---|---|---|---|---|
| | 9 | 10 | 11 | 12 |
| DPH (mg/ml) | a) 25-75<br>b) 75-125<br>c) 125-250<br>d) 250-500 | a) 25-75<br>b) 75-125<br>c) 125-250<br>d) 250-500 | a) 25-75<br>b) 75-125<br>c) 125-250<br>d) 250-500 | a) 25-75<br>b) 75-125<br>c) 125-250<br>d) 250-500 |
| PEG (w/w) | 0-30% | 0-30% | 0-30% | 0-30% |
| PPG (w/w) | 1-10% | 10-15% | 15-20% | 20-30% |
| Gly. (w/w) | 0% | 0% | 0% | 0% |
| AA (w/w) | 0.1-1% | 0.1-1% | 0.1-1% | 0.1-1% |
| Pres. (w/w) | 0.1-1% | 0.1-1% | 0.1-1% | 0.1-1% |
| PE (w/w) | 0-5% | 0-5% | 0-5% | 0-5% |
| VM (w/w) | 0-5% | 0-5% | 0-5% | 0-5% |
| IA (w/w) | 0-5% | 0-5% | 0-5% | 0-5% |
| pH range | 3-6 | 3-6 | 3-6 | 3-6 |

TABLE 4

Compositions of Formulations 13a-16d

| | Formulation Number | | | |
|---|---|---|---|---|
| | 13 | 14 | 15 | 16 |
| DPH (mg/ml) | a) 25-75<br>b) 75-125<br>c) 125-250<br>d) 250-500 | a) 25-75<br>b) 75-125<br>c) 125-250<br>d) 250-500 | a) 25-75<br>b) 75-125<br>c) 125-250<br>d) 250-500 | a) 25-75<br>b) 75-125<br>c) 125-250<br>d) 250-500 |
| PEG (w/w) | 0-30% | 0-30% | 0-30% | 0-30% |
| PPG (w/w) | 0% | 0% | 0% | 0% |
| Gly. (w/w) | 1-10% | 10-15% | 15-20% | 20-30% |
| AA (w/w) | 0.1-1% | 0.1-1% | 0.1-1% | 0.1-1% |
| Pres. (w/w) | 0.1-1% | 0.1-1% | 0.1-1% | 0.1-1% |
| PE (w/w) | 0-5% | 0-5% | 0-5% | 0-5% |
| VM (w/w) | 0-5% | 0-5% | 0-5% | 0-5% |
| IA (w/w) | 0-5% | 0-5% | 0-5% | 0-5% |
| pH range | 3-6 | 3-6 | 3-6 | 3-6 |

TABLE 5

Compositions of Formulations 17a-20d

| | Formulation Number | | | |
|---|---|---|---|---|
| | 17 | 18 | 19 | 20 |
| DPH (mg/ml) | a) 25-75<br>b) 75-125<br>c) 125-250<br>d) 250-500 | a) 25-75<br>b) 75-125<br>c) 125-250<br>d) 250-500 | a) 25-75<br>b) 75-125<br>c) 125-250<br>d) 250-500 | a) 25-75<br>b) 75-125<br>c) 125-250<br>d) 250-500 |
| PEG (w/w) | 0-30% | 0-30% | 0-30% | 0-30% |
| Solv. (w/w) | 0-30% | 0-30% | 0-30% | 0-30% |
| AA (w/w) | 0.1-1% | 0.1-1% | 0.1-1% | 0.1-1% |
| Pres. (w/w) | 0.1-1% | 0.1-1% | 0.1-1% | 0.1-1% |
| $PE^A$ (w/w) | 0.1-0.5% | 0.5-1% | 1-1.5% | 1.5-2.0% |
| $PE^B$ (w/w) | 0% | 0% | 0% | 0% |
| VM (w/w) | 0-5% | 0-5% | 0-5% | 0-5% |
| IA (w/w) | 0-5% | 0-5% | 0-5% | 0-5% |
| pH range | 3-6 | 3-6 | 3-6 | 3-6 |

TABLE 6

Compositions of Formulations 21a-24d

| | Formulation Number | | | |
|---|---|---|---|---|
| | 21 | 22 | 23 | 24 |
| DPH (mg/ml) | a) 25-75<br>b) 75-125<br>c) 125-250<br>d) 250-500 | a) 25-75<br>b) 75-125<br>c) 125-250<br>d) 250-500 | a) 25-75<br>b) 75-125<br>c) 125-250<br>d) 250-500 | a) 25-75<br>b) 75-125<br>c) 125-250<br>d) 250-500 |
| PEG (w/w) | 0-30% | 0-30% | 0-30% | 0-30% |
| Solv. (w/w) | 0-30% | 0-30% | 0-30% | 0-30% |
| AA (w/w) | 0.1-1% | 0.1-1% | 0.1-1% | 0.1-1% |
| Pres. (w/w) | 0.1-1% | 0.1-1% | 0.1-1% | 0.1-1% |
| $PE^A$ (w/w) | 0% | 0% | 0% | 0% |
| $PE^B$ (w/w) | 0.1-0.5% | 0.5-1% | 1-1.5% | 1.5-2.0% |
| VM (w/w) | 0-5% | 0-5% | 0-5% | 0-5% |
| IA (w/w) | 0-5% | 0-5% | 0-5% | 0-5% |
| pH range | 3-6 | 3-6 | 3-6 | 3-6 |

TABLE 7

Compositions of Formulations 25a-28d

| | Formulation Number | | | |
|---|---|---|---|---|
| | 25 | 26 | 27 | 28 |
| DPH (mg/ml) | a) 25-75 b) 75-125 c) 125-250 d) 250-500 | a) 25-75 b) 75-125 c) 125-250 d) 250-500 | a) 25-75 b) 75-125 c) 125-250 d) 250-500 | a) 25-75 b) 75-125 c) 125-250 d) 250-500 |
| PEG (w/w) | 0-30% | 0-30% | 0-30% | 0-30% |
| Solv. (w/w) | 0-30% | 0-30% | 0-30% | 0-30% |
| AA (w/w) | 0.1-1% | 0.1-1% | 0.1-1% | 0.1-1% |
| Pres. (w/w) | 0.1-1% | 0.1-1% | 0.1-1% | 0.1-1% |
| $PE^C$ (w/w) | 0.1-0.5% | 0.5-1% | 1-1.5% | 1.5-2.0% |
| $PE^D$ (w/w) | 0% | 0% | 0% | 0% |
| VM (w/w) | 0-5% | 0-5% | 0-5% | 0-5% |
| IA (w/w) | 0-5% | 0-5% | 0-5% | 0-5% |
| pH range | 3-6 | 3-6 | 3-6 | 3-6 |

TABLE 8

Compositions of Formulations 29a-32d

| | Formulation Number | | | |
|---|---|---|---|---|
| | 29 | 30 | 31 | 32 |
| DPH (mg/ml) | a) 25-75 b) 75-125 c) 125-250 d) 250-500 | a) 25-75 b) 75-125 c) 125-250 d) 250-500 | a) 25-75 b) 75-125 c) 125-250 d) 250-500 | a) 25-75 b) 75-125 c) 125-250 d) 250-500 |
| PEG (w/w) | 0-30% | 0-30% | 0-30% | 0-30% |
| Solv. (w/w) | 0-30% | 0-30% | 0-30% | 0-30% |
| AA (w/w) | 0.1-1% | 0.1-1% | 0.1-1% | 0.1-1% |
| Pres. (w/w) | 0.1-1% | 0.1-1% | 0.1-1% | 0.1-1% |
| $PE^C$ (w/w) | 0% | 0% | 0% | 0% |
| $PE^D$ (w/w) | 0.1-0.5% | 0.5-1% | 1-1.5% | 1.5-2.0% |
| VM (w/w) | 0-5% | 0-5% | 0-5% | 0-5% |
| IA (w/w) | 0-5% | 0-5% | 0-5% | 0-5% |
| pH range | 3-6 | 3-6 | 3-6 | 3-6 |

EXAMPLES

The following examples are for the purpose of illustration of the present disclosure only and are not intended to limit the scope of the present disclosure in any manner whatsoever.

Example 1—Assessment of Mucin Binding to Diphenhydramine

The objective of this study was to determine the percent binding of diphenhydramine to mucin at pH 5.5, using equilibrium dialysis.

Studies were carried out in mucin (Sigma-Aldrich, Cat #M1778). Mucin was first dissolved into pH 5.5 potassium biphthalate buffer at a final concentration of 2.5% mucin. A Pierce Rapid Equilibrium Dialysis (RED) device was used for the experiments. A stock solution of diphenhydramine (Sigma-Aldrich, Cat #D3630) was prepared at 10 mM in DMSO. Aliquots of the DMSO solution were dosed into 1.0 mL of mucin solution at a dosing concentration of 10 µM for diphenhydramine. In triplicate, aliquots (300 µL) of this solution were loaded into three wells of a 96-well dialysis plate. Potassium biphthalate buffer (500 µL, pH 5.5) was added to each corresponding receiver chamber. The device was then placed into an enclosed heated rocker that was pre-warmed to 37° C., and allowed to incubate for four hours. After 4 hours of incubation, both sides were sampled.

Aliquots (50 µL for donor, 200 µL for receiver) were removed from the chambers and placed into a 96-well plate. Mucin solution (50 µL) was added to the wells containing the receiver samples, and 200 µL of potassium biphthalate was added to the wells containing the donor samples. Two volumes of acetonitrile (ACN) were added to each well, and the plate was mixed and then centrifuged at 3,000 rpm for 10 minutes. Aliquots of the supernatant were removed, diluted 1:1 into water containing analytical internal standard (deuterium labeled diphenhydramine), and analyzed by LC-MS/MS. Calibration standards were prepared in a matched matrix and prepared similarly to the assay samples.

Binding and recovery values were calculated as follows:

% Bound=[(Concentration in Donor−Concentration in Receiver)/(Concentration in Donor)]×100%

Recovery=[(Concentration in Donor+Concentration in Receiver)/(Nominal Dosing Concentration)]×100

The results are provided below in Table 9, and demonstrate that diphenhydramine hydrochloride does not substantially bind to the main protein in the nasal membrane.

TABLE 9

DPH Binding and Recovery Data

| | | % Bound | | | | % Recovery | | | |
|---|---|---|---|---|---|---|---|---|---|
| Test Article | Matrix | R1 | R2 | R3 | Mean (StDev) | R1 | R2 | R3 | Mean (StDev) |
| Diphenhydramine | 2.5% Mucin | 25.1 | 23.6 | 24.4 | 24.4(3.0) | 109 | 109 | 106 | 108(1.9) |

Example 2—Unidirectional Permeability of Diphenhydramine in Mattek EpiAirway Respiratory Tissues The test article, diphenhydramine, and reference compounds atenolol and caffeine were purchased from Sigma-Aldrich (St. Louis, Mo.).

EpiAirway™ tissues, plated in 24-well plates, and accompanying culture medium and assay buffer solutions, were purchased from MatTek Corporation (Ashland, Mass.). According to the EpiAirway™ AIR-100 Use Protocol provided by MatTek, the tissues were returned to culture immediately upon receipt. In a tissue culture hood, using sterile technique, 1.0 mL of cold medium (AIR-100-ASY) was dispensed into each well of the 6-well plate (n=3) and one tissue insert was transferred to each of the wells. The apical surface of the tissue was exposed to the air (no medium was added to the insert). The tissues were equilibrated overnight at 37° C. in a 5% $CO_2$ incubator. The culture medium was then replaced with fresh, pre-warmed medium until use.

Mass spectrometer (MS) conditions were optimized for sensitivity of test article detection, and liquid chromatography (LC) conditions were optimized for separation of the test article from matrix interference, using a standard reverse-phase column and gradient method.

Non-specific binding (NSB) assessment was conducted with tissue-free membranes in the EpiAirway apparatus (see details in Table 4) provided by MatTek. Diphenhydramine was tested at 100 μM, according to protocol 18APCIP2. The assay buffer used for both the donor and receiver sides was DPBS, 7.4. The receiver chamber was sampled at 120 minutes, and the donor side was sampled at 0 and 120 minutes. NSB assessment takes into account mass balance recovery to determine whether a test article binds non-specifically to the experimental device.

The unidirectional permeation experiment was conducted according to protocol 18APCIP2 and relevant SOPs of Absorption Systems. Prior to the permeability assay, the culture medium in the plate was aspirated; and ~1 mL of Dulbecco's phosphate-buffered saline (DPBS) was added to the well to remove any remaining residue of culture medium from the underside of the insert. The tissues were transferred to a 24-well plate with DPBS (750 μL) in each well as receiver, and dosing solution (400 μL) was added to each insert. A 100 μL aliquot was immediately removed as the 0-minute donor sample. Receiver samples (200 μL) were collected at 30, 60, and 120 minutes, replaced with an equal volume of fresh pre-warmed blank buffer at 30 and 60 minutes. The donor side was sampled (100 μL) at 0 and 120 minutes. The assay plate was placed in a humidified $CO_2$ incubator at 37° C. during the assay period.

After 120 minutes, the tissues were rinsed with DPBS and gently dried with tissue wipes after aspiration of the assay buffer. The insert membranes with tissues attached were carefully removed from the insert apparatus, placed in a tared centrifuge tube, and weighed. To extract accumulated diphenhydramine from the tissues, 0.5 mL of acetonitrile was added to each tube for 10 minutes at room temperature, and 0.3 mL of lysate was sampled for analysis.

The details of the treatments are summarized below in Table 10. Atenolol was used as a marker of low permeability, while caffeine was used as a marker of high permeability.

TABLE 10

Summary of Treatments for Unidirectional Permeability

| Treatment | Assay Buffer (pH) | Analytes | Sampling Time Points |
|---|---|---|---|
| Diphenhydramine (100 μM), Atenolol (100 μM), and Caffeine (50 μM) | DPBS (7.4) | Diphenhydramine, Atenolol & Caffeine | Donors: 0 and 120 min; Receivers: 30, 60, and 120 min |

Sample and Data Analysis

The test article and reference compounds were assayed by LC-MS/MS.

The apparent permeability coefficient ($P_{app}$) and recovery were calculated as follows:

$$P_{app}=(dC_r/dt) \times V_r/(A \times C_{ini}) \quad (1)$$

$$\text{Recovery (\%)}=[((C_{r,final} \times V_r)+(C_{d,final} \times V_d))/(C_{ini} \times V_d)] \times 100 \quad (2)$$

$$\text{Recovery (\%)}=[((C_{r,final} \times V_r)+(C_{d,final} \times V_d)+(\text{Tissue Accumulation}))/(C_{ini} \times V_d)] \times 100 \quad (3)$$

where, $dC_r/dt$ is the slope of cumulative receiver concentration vs. time in μM s$^{-1}$;

$V_r$ is the volume of the receiver compartment;

$V_d$ is the volume of the donor compartment;

A is the diffusional area of the membrane;

$C_{ini}$ is the donor concentration at 0 minutes in μM;

$C_{D,final}$ is the donor concentration at 120 minutes in μM;

$C_{r,final}$ is the receiver concentration at 120 minutes in μM.

Equation (2) was used for atenolol and caffeine, and Equation (3) was used for diphenhydramine.

NSB was evaluated in tissue-free inserts with the same buffer (DPBS) used in the permeability assay, and the results are provided below in Table 11. The average recovery of diphenhydramine was 86.3% in the tissue-free inserts, and the cell-free $P_{app}$ across the tissue-free membrane was 26.6× 10$^{-6}$ cm/s. The results indicate that there is little NSB of diphenhydramine to the experimental device.

TABLE 11

Non-Specific Binding of Diphenhydramine

| | | $P_{app}$ | | | | Average |
|---|---|---|---|---|---|---|
| Inserts | Test Article | R1 | R2 | R3 | Average ± SD | Recovery (%) |
| Milcel-ECM Tissue-free Insert | Diphen-hydramine | 26.3 | 26.7 | 26.6 | 26.6 ± 0.188 | 86.3 |

Unidirectional (dosing from the apical side) permeation assessment for diphenhydramine (dosed at 100 μM) across EpiAirway tissues was conducted according to the protocol, with co-dosed reference compounds atenolol (100 μM) and caffeine (50 μM). With DPBS, pH 7.4 used on both the donor and receiver sides, permeability was initiated with addition of 0.4 mL of dosing solution into the inserts and of 0.75 mL of blank buffer into the wells of the assay plate. The assay was performed for 120 minutes in a humidified incubator at 37° C.

As provided below in Table 12, $P_{app}$ values of $0.224 \times 10^{-6}$ cm/s for the low permeability marker atenolol, and $29.1 \times 10^{-6}$ cm/s for the high permeability marker caffeine, were observed. Accordingly, the $P_{app}$ ratio ($P_{app\_caffeine}/P_{app\_atenolol}$) was determined to be 130. These results indicate the appropriate function of the batch of EpiAirway tissues, as low-permeability and high-permeability compounds are clearly distinguished.

As also provided in Table 12, the permeability of diphenhydramine (average $P_{app}=27.6 \times 10^{-6}$ cm/s) was found to be similar to that of caffeine (average $P_{app}=29.1 \times 10^{-6}$ cm/s). Thus, like caffeine, diphenhydramine has high absorption potential.

TABLE 12

Permeability Coefficient and Recovery of Test Articles Across EpiAirway Tissues

| | $P_{app}$ ($10^{-6}$ cm/s) | | | | Average Recovery | $P_{app}$ |
|---|---|---|---|---|---|---|
| Analyte | R1 | R2 | R3 | Average ± SD | (%) | Ratio[a] |
| Atenolol | 0.159 | 0.252 | 0.261 | 0.224 ± 0.0566 | 98.5 | 130 |
| Caffeine | 30.9 | 28.2 | 28.2 | 29.1 ± 1.56 | 96.9 | |
| Diphen-hydramine | 31.5 | 25.8 | 25.6 | 27.6 ± 3.34 | 103 | N.A. |

[a]$P_{app}$ ratio = ($P_{app\_caffeine}/P_{app\_atenolol}$); the value should be ≥ 2.

In addition, as provided below in Table 13, accumulation of diphenhydramine was similar in the three tissue replicates, which was taken into account when calculating the recovery of diphenhydramine.

TABLE 13

Accumulation of Diphenhydramine in EpiAirways Tissues

| | Tissue Accumulation (nmol/mg) | | | |
|---|---|---|---|---|
| Analyte | R1 | R2 | R3 | Average ± SD |
| Diphenhydramine | 0.188 | 0.231 | 0.218 | 0.212 ± 0.0222 |

Example 3—Intranasal Administration of Diphenhydramine to Rats

The pharmacokinetics of DPH were evaluated in fasted male Sprague-Dawley rats. Diphenhydramine hydrochloride was formulated at 0.357 mg/mL and 25 mg/mL in 50 mM acetate buffer for intravenous (IV) and intranasal (IN) dosing, respectively. The dosing formulations were prepared fresh on the day of dosing.

Surgically modified rats were housed one per cage. Rats intended for IN dosing had one jugular vein cannula (JVC) for sample collection. Rats intended for IV dosing were fitted with two jugular vein cannulas (JVC/JVC) for dosing and sample collection, respectively. IV dosing was performed in triplicate, while IN dosing was performed in sextuplicate.

Rats were fasted for a minimum of twelve hours prior to formulation administration.

Food was returned at four hours post dosing. Animals had free access to water throughout the study. Each rat received either a single bolus IV injection via a JVC or a single intranasal dose via pipette.

Blood samples (0.25 mL) were collected from the JVC and placed into chilled tubes containing sodium heparin, inverted several times to mix, and kept on ice until centrifugation. The samples were then centrifuged at 3,000×g for 5 minutes at a temperature of 2 to 8° C. Plasma was collected into polypropylene tubes after centrifugation and then frozen on dry ice, until they were transferred to a freezer maintained at −60° C. to −80° C. pending analysis.

Figure 2:
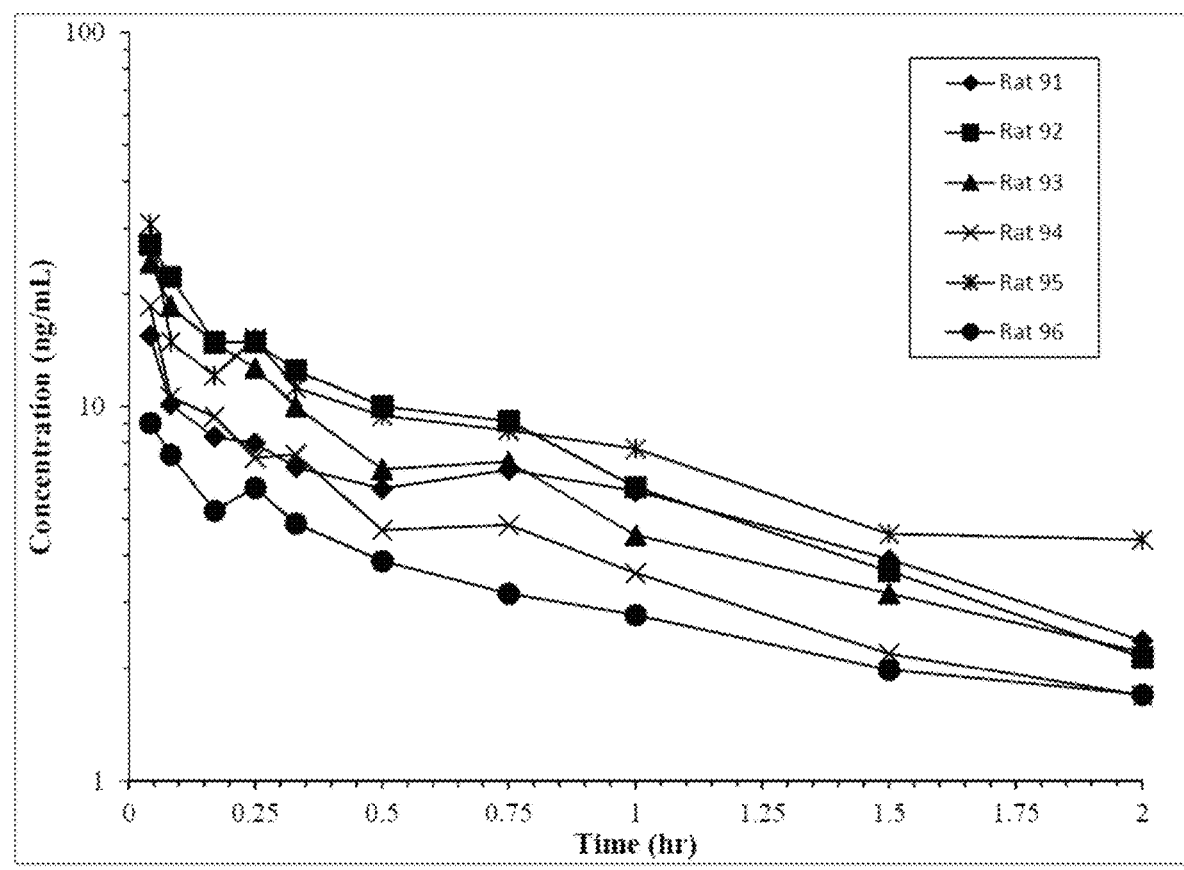
FIG. 2 depicts plasma concentrations arising after intranasal administration of diphenhydramine (0.357 mg/kg) to male Sprague-Dawley rats.

Individual plasma concentrations and pharmacokinetic parameters of DPH are shown graphically in FIG. 1 (IV dosing) and FIG. 2 (IN dosing). The PK data is provided below in Tables 14 and 15, where DPH concentrations are expressed as ng/mL of free drug in Table 15. Samples that were below the limit of quantitation (1.00 ng/mL) were not used in the calculation of averages.

TABLE 14

Pharmacokinetic data for IV and IN administration

| Group # | Test Article | Dosing Route | Total Animals N= | Dose (mg/kg) | Dosing Solution Conc. (mg/mL) | Dosing Volume (mL/kg) | Vehicle | Sampling Time Points |
|---|---|---|---|---|---|---|---|---|
| 1 | DPH | IV | 3 | 0.357 | 0.357 | 1 | 50 mM Acetate buffer* | Pre-dose(0), 2.5, 5, 10, 15, 20, 30, |
| 2 | | IN | 6 | 0.357 | 25 | 0.01428 | 50 mM Acetate buffer* | 45 min, 1, 1.5, and 2 hrs |

*Adjust to pH 5.5

TABLE 15

Pharmacokinetic data for IV and IN administration

|  | $C_{max}$ IV (ng/mL) (n = 3) | $C_{max}$ IN (ng/mL) (n = 6) | $AUG_\infty$, IV (hr · ng/mL) (n = 3) | $AUG_\infty$, IN (hr · ng/mL) (n = 6) |
| --- | --- | --- | --- | --- |
|  | 64.9 | 15.5 | 30.1 | 11.2 |
|  | 67.8 | 27.2 | 32 | 15.6 |
|  | 79.2 | 24.3 | 34.1 | 12.7 |
|  |  | 18.6 |  | 8.8 |
|  |  | 30.8 |  | 16.3 |
|  |  | 9.03 |  | 6.45 |
| Mean | 70.6 | 20.9 | 32.1 | 11.8 |
| SD | 7.6 | 8.1 | 2.0 | 3.8 |
| % CV | 10.7 | 38.5 | 6.2 | 32.4 |

The relative bioavailability of DPH delivered by IN dosing (29.6% of $C_{max}$ IV; 36.8% of $AUC_\infty$ IV) indicates that intranasal administration is a viable delivery method for achieving clinically relevant plasma concentrations of DPH, and is understood to be far more convenient than intravenous administration.

Example 4—Intranasal Administration of DPH Along with Penetration Enhancers

The effects of penetration enhancers upon IN absorption of DPH were compared to IN administration of DPH in buffer vehicle alone (50 mM Acetate Buffer, pH 5.5). Three different classes of enhancers were investigated, as listed in Table 16 below.

TABLE 16

Penetration Enhancers Listed by Category and Name

| Category | Enhancer |
| --- | --- |
| Fatty Acids | Sodium Caprate 1% |
| Positive Charged Polymers | Chitosan oligosaccharide 0.5% |
| Surfactants (Anionic) | Sodium Lauryl Sulfate 0.5% |

An un-anesthetized rat model was used. A dose of 0.357 mg/kg of DPH was administered for all IN groups. Systemic exposure was assessed by measuring DPH plasma levels at 0 minute (pre-dose) and at 1, 2.5, 5, 10, 15, 20, 30, and 60 minutes post-IN administration. A CSF sample was taken after the last blood sample at 60 minutes. Each IN group consisted of four rats. In addition, a control group of where DPH was administered in 50 mM acetate buffer pH 5.5 vehicle, as well as an IV group consisting of three rats where DPH was administered intravenously, were tested.

Systemic exposure of DPH was assessed by comparing $AUC_{last}$ and $C_{max}$ values. The comparative systemic exposure for each enhancer to the systemic exposure of the buffer vehicle was assessed.

Results for IN Buffer Group

Following IN dosing of rats with DPH in a 50 mM acetate buffer (pH 5.5) formulation, the mean maximum plasma concentration was 9.34 ng/ml with a median $T_{max}$ of 2.5 minutes post dosing. The mean systemic exposure based on the $AUC_{last}$ was 5.17 hr*ng/mL. The average CSF concentrations at the 60 minute timepoint was 3.82 ng/mL.

Results for IN Sodium Caprate Group

Following IN dosing of DPH in 1% sodium caprate/50 mM acetate buffer formulation mean maximum plasma concentration was determined to be 16.0 ng/mL, with a median $T_{max}$ of 1.8 minutes post dosing. The $C_{max}$ value for the sodium caprate group was 71% higher than the vehicle group. The mean systemic exposure based on the $AUC_{last}$ was 5.73 hr*ng/mL. The average CSF concentrations at 60 minutes was 4.03 ng/mL.

Figure 3:
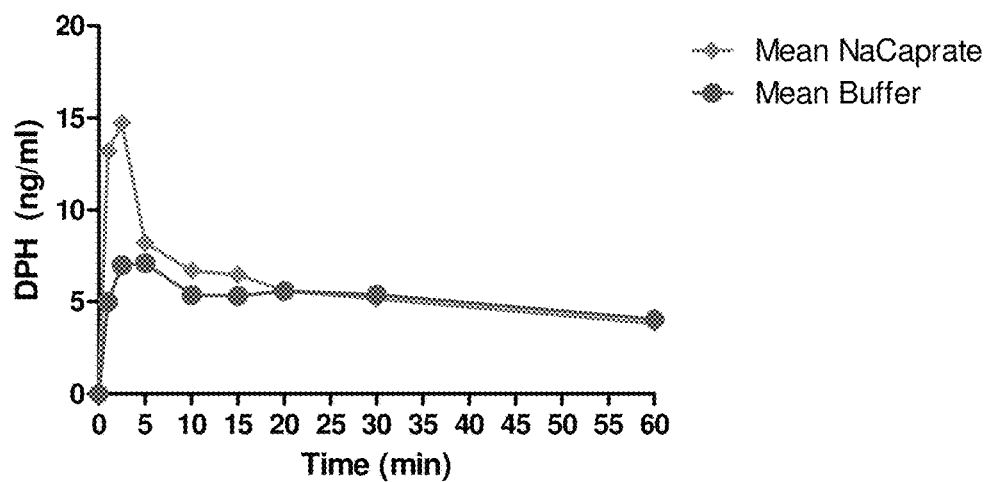
FIG. 3 depicts plasma concentrations of DPH administered intranasally with and without sodium caprate.
Figure 4:
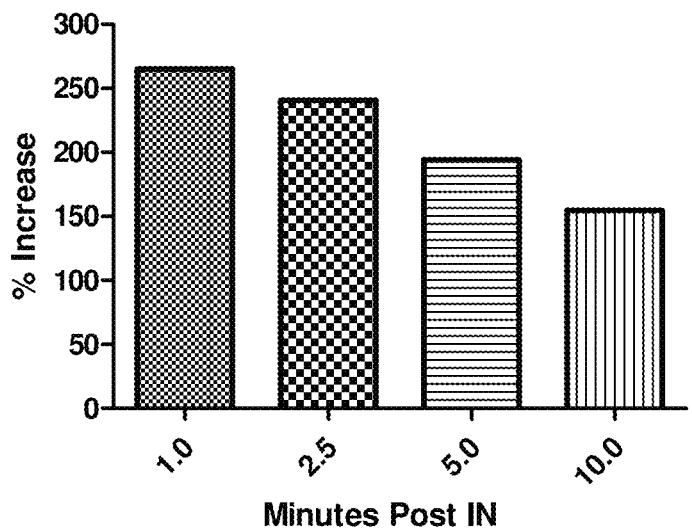
FIG. 4 depicts the increase in plasma concentration when DPH is administered intranasally in combination with sodium caprate relative to buffer.

A comparison of the mean sodium caprate DPH plasma profile to the mean Buffer DPH plasma profile is shown in FIG. 3. The relative percent increase of the AUC of the drug in the sodium caprate group over that of the buffer group at the 1, 2.5, 5, and 10 minute post-dose timepoints are shown in FIG. 4. It is observed that the percent increase at 1 minute of the sodium caprate group was 265% higher than that of the buffer group, and remained at least 150% higher out to 10 minutes post dose.

Also, sodium caprate CSF levels were measured at 60 minutes post dose, well beyond the 1-minute highest systemic exposure for sodium caprate relative to the buffer. As a result, the relative CNS exposure may be substantially underestimated. The CSF level at sixty minutes post dose for the IN sodium caprate corresponds to a 5.5% increase over buffer CSF.

Results for IN Sodium Lauryl Sulfate Group

Following IN dosing of DPH in a 0.5% sodium lauryl sulfate/50 mM acetate buffer formulation, the mean maximum plasma concentration was determined to be 10.5 ng/mL, with a median $T_{max}$ of 1.8 minutes post dosing. The $C_{max}$ value for the sodium lauryl sulfate group was 12% higher than the buffer group. The mean systemic exposure based on the $AUC_{last}$ was 6.40 hr*ng/mL. The average CSF concentrations at sixty minutes was 5.65 ng/mL.

Figure 5:
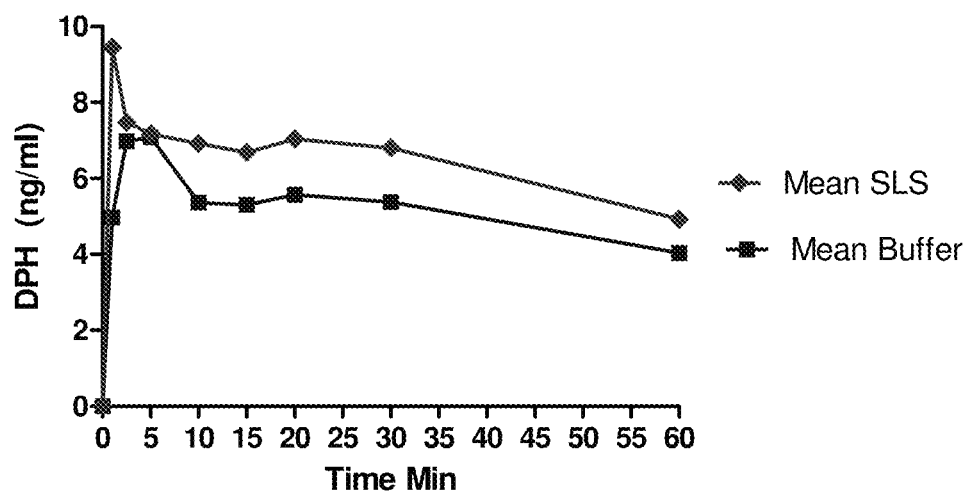
FIG. 5 depicts plasma concentrations of DPH administered intranasally with and without sodium lauryl sulfate.
Figure 6:
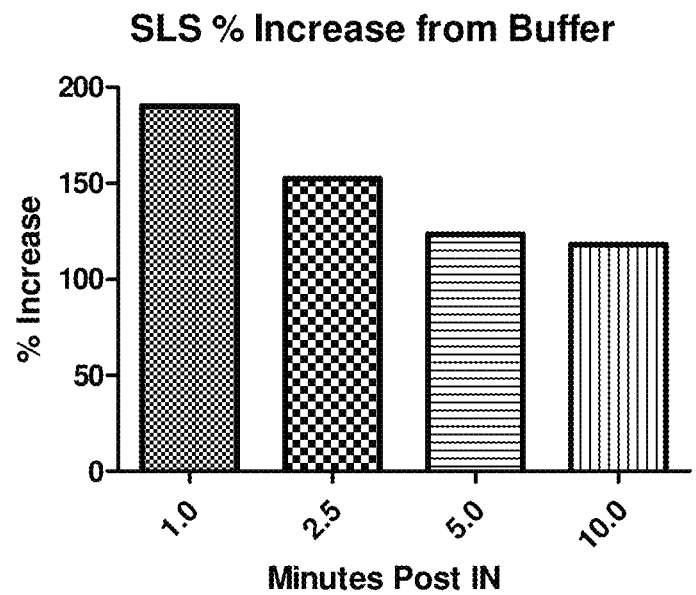
FIG. 6 depicts the increase in plasma concentration when DPH is administered intranasally in combination with sodium lauryl sulfate relative to buffer.

A comparison of the mean sodium lauryl sulfate DPH plasma profile to the mean Buffer DPH plasma profile is shown in FIG. 5. The relative percent increase of the AUC of the drug in the sodium lauryl sulfate group over that of the buffer group in AUC at the 1, 2.5, 5, and 10 minute post-dose timepoints are shown in FIG. 6.

Also, sodium lauryl sulfate CSF levels were measured at 60 minutes post-dose, well beyond the 1-minute highest systemic exposure for sodium lauryl sulfate relative to the buffer. As a result, the relative CNS exposure may be substantially underestimated. The CSF at 60 minutes post-dose for the IN sodium lauryl sulfate was 5.65 ng/mL, corresponding to a 48% increase over buffer.

Results for IN Chitosan Oligosaccharide Group

Following IN dosing of DPH in a 0.5% chitosan oligosaccharide/50 mM acetate buffer formulation, the mean maximum plasma concentration was determined to be 10.4 ng/mL, with a median $T_{max}$ of 5 minutes post dosing. The $C_{max}$ value for the chitosan oligosaccharide group was 11% higher than the buffer group. The mean systemic exposure based on the $AUC_{last}$ was 5.80 hr*ng/mL. The average CSF concentrations at sixty minutes was 5.26 ng/mL.

Figure 7:
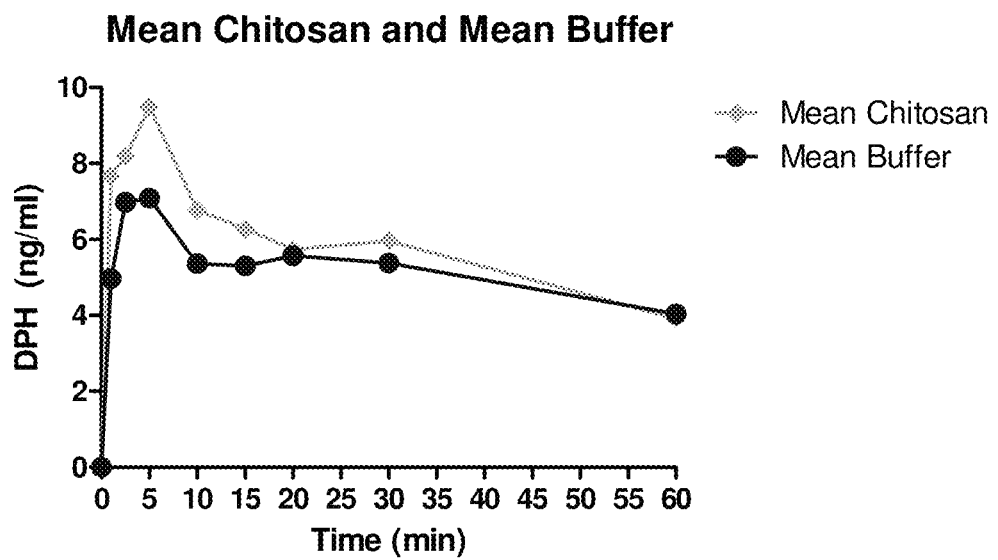
FIG. 7 depicts plasma concentrations of DPH administered intranasally with and without chitosan oligosaccharide.
Figure 8:
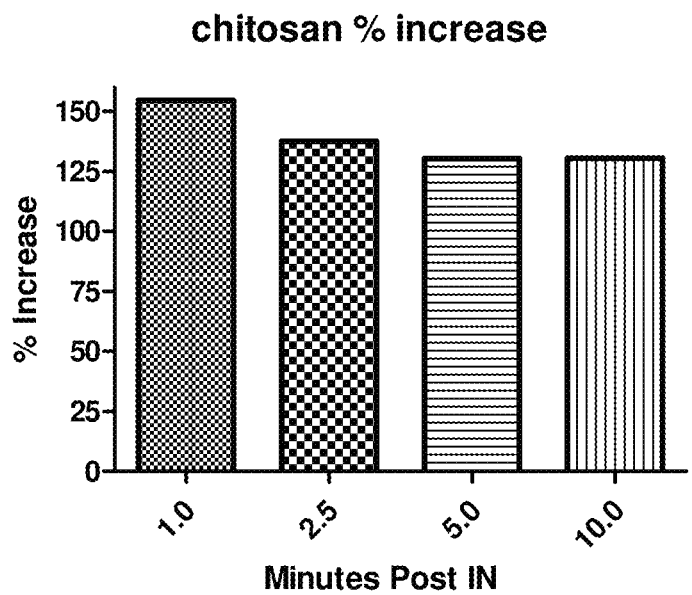
FIG. 8 depicts the increase in plasma concentration when DPH is administered intranasally in combination with chitosan oligosaccharide relative to buffer.

A comparison of the mean chitosan oligosaccharide DPH plasma profile to the mean buffer DPH plasma profile is shown in FIG. 7. The relative percent increase of the AUC of the drug in the chitosan oligosaccharide group over the buffer group at the 1, 2.5, 5, and 10 minute post-dose timepoints are shown in FIG. 8.

Also, chitosan oligosaccharide CSF levels were measured at 60 minutes post-dose, well beyond the 5-minute highest systemic exposure for chitosan oligosaccharide relative to the buffer. As a result, the relative CNS exposure may be substantially underestimated. The CSF at 60 minutes post dose for the IN chitosan oligosaccharide was 5.26 ng/mL, corresponding to a 37% increase over buffer.

The mean PK parameters for the IN buffer group and the three enhancer IN groups are provided below in Table 17. Also, cumulative AUC values over time for the four cohorts are provided below in Table 18.

TABLE 17

Mean PK Parameters Following IN Treatment with DPH and a Penetration Enhancer, or DPH in Buffer

| Enhancer | Mean $C_{max}$ (ng/mL) | Mean $AUC_{last}$ (hr · ng/mL) | Median $T_{max}$ (min) |
|---|---|---|---|
| Sodium Lauryl sulfate 0.5% | 10.5 | 6.4 | 1.8 |
| Chitosan Oligosaccharide 0.5% | 10.4 | 5.8 | 5 |
| Sodium Caprate 1% | 16.0 | 5.73 | 1.8 |
| Buffer 50 mM Acetate | 9.34 | 5.17 | 2.5 |

TABLE 18

Mean Cumulative AUC Following IN Treatment with DPH and a Penetration Enhancer, or DPH in Buffer

| Time (min) | Mean Buffer (hr · ng/mL) | Mean Sodium Caprate (hr · ng/mL) | Mean Chitosan (hr · ng/mL) | Mean Sodium Lauryl Sulfate (hr · ng/mL) |
|---|---|---|---|---|
| 0 | 0 | 0.00 | 0 | 0 |
| 1 | 0.04 | 0.11 | 0.07 | 0.08 |
| 2.5 | 0.19 | 0.46 | 0.26 | 0.29 |
| 5 | 0.48 | 0.93 | 0.63 | 0.59 |
| 10 | 1.02 | 1.58 | 1.33 | 1.21 |
| 15 | 1.45 | 2.10 | 1.86 | 1.75 |
| 20 | 1.88 | 2.59 | 2.34 | 2.30 |
| 30 | 2.81 | 3.50 | 3.33 | 3.47 |
| 60 | 5.17 | 5.73 | 5.80 | 6.40 |

A plot of the mean cumulative AUC for the three enhancers and buffer vs. time post-IN administration is shown in FIG. 8. FIG. 8 shows that all three penetration enhancers had greater systemic exposure than buffer alone out to 60 minutes postIN administration.

Results for IV Buffer Group

IV dosing of rats with DPH in a 50 mM acetate buffer (pH 5.5) formulation resulted in a mean $C_0$ (maximum plasma concentration) of 64.7 ng/mL. The mean $AUC_{last}$ was 21.8 hr*ng/mL, and the mean CSF concentration at 60 minutes was 8.2 ng/mL.

Figure 9:
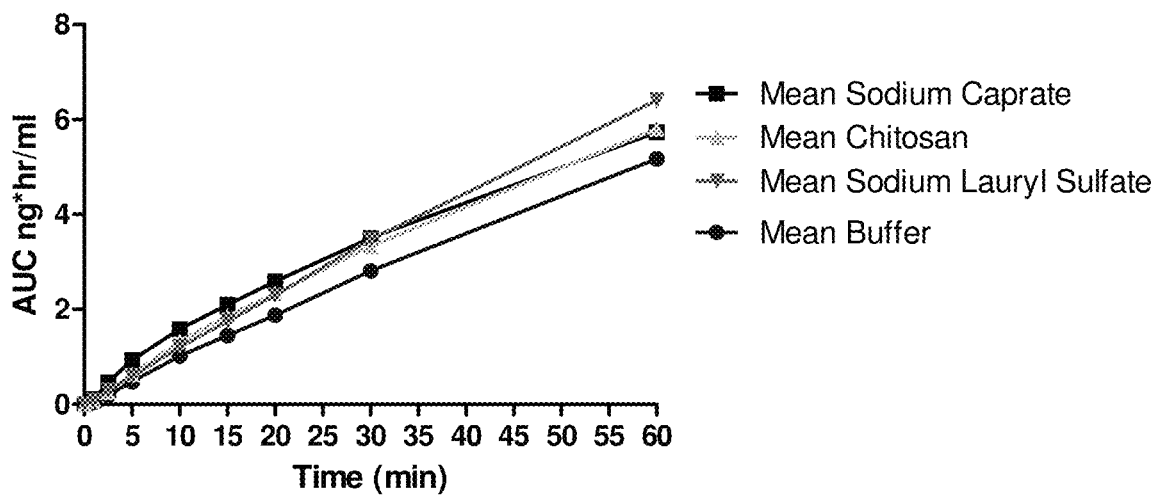
FIG. 9 depicts plasma concentrations after intranasal administration of DPH with certain penetration enhancers compared to buffer.
Figure 10:
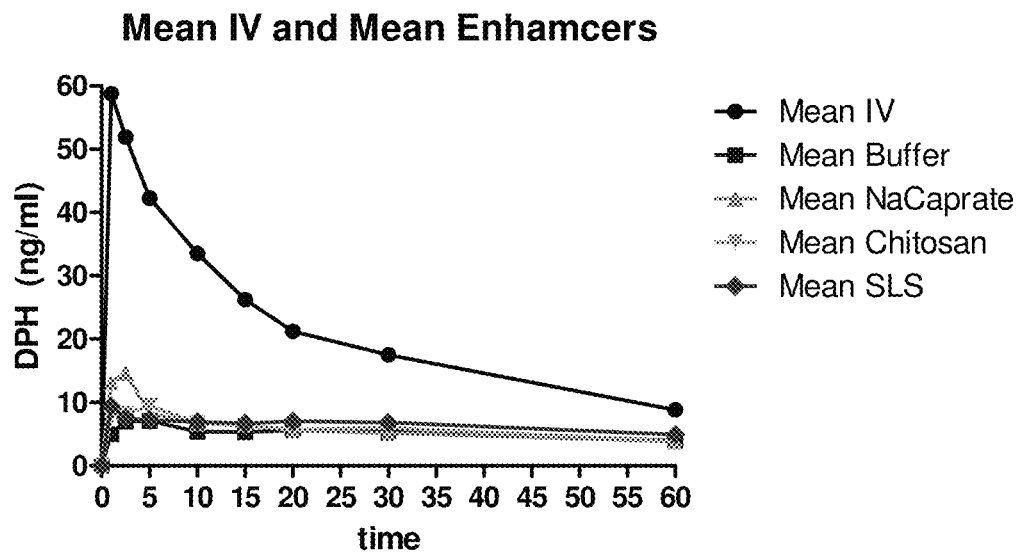
FIG. 10 depicts plasma concentrations after intravenous administration and intranasal administration of DPH.

Example 5—Comparison of IV DPH Administration to IN DPH Administration, with or without Penetration Enhancers FIG. 9 compares the mean IV DPH plasma profile to the mean IN DPH plasma profiles for dosing with sodium caprate, sodium lauryl sulfate, chitosan oligosaccharide, and buffer (see Example 4). The mean DPH concentrations at each of the 0, 1, 2.5, 5, 10, 15, 20, 30, and 60 minute timepoints for the IV-dosed buffer group, the three IN-dosed enhancer groups, and the IN-dosed buffer group are provided below in Table 19. The mean $AUC_{last}$ values for all five cohorts are provided below in Table 20.

TABLE 19

Comparison of Mean DPH Concentration (ng/mL) for IN-Administered Enhancers, IN-Administered Buffer, and IV-Administered Buffer

| Time Min | Mean IV Buffer | Mean IN Buffer | Mean Na Caprate | Mean Chitosan | Mean SLS |
|---|---|---|---|---|---|
| 0 | 0 | 0 | 0 | 0 | 0 |
| 1 | 58.8 | 4.97 | 13.2 | 7.68 | 9.45 |
| 2.5 | 51.9 | 6.98 | 14.7 | 8.17 | 7.49 |
| 5 | 42.3 | 7.09 | 8.21 | 9.49 | 7.17 |
| 10 | 33.5 | 5.36 | 6.68 | 6.78 | 6.92 |
| 15 | 26.2 | 5.30 | 6.46 | 6.28 | 6.68 |
| 20 | 21.2 | 5.57 | 5.57 | 5.74 | 7.04 |
| 30 | 17.5 | 5.38 | 5.15 | 5.96 | 6.8 |
| 60 | 8.81 | 4.04 | 3.81 | 3.91 | 4.93 |

TABLE 20

Comparison of Mean $AUC_{last}$ for IN-Administered Enhancers, IN-Administered Buffer, and IV-Administered Buffer

| | Sodium Lauryl Sulfate hr*ng/mL | Chitosan oligosaccharide hr*ng/mL | Sodium Caprate hr*ng/mL | IN Buffer hr*ng/mL | IV Buffer hr*ng/mL |
|---|---|---|---|---|---|
| MEAN | 6.4 | 5.8 | 5.73 | 5.17 | 21.8 |
| St Dev | 3.67 | 1.09 | 3.93 | 2.46 | 2.76 |
| % CV | 57.3 | 18.8 | 68.6 | 47.6 | 12.7 |

Figure 11:
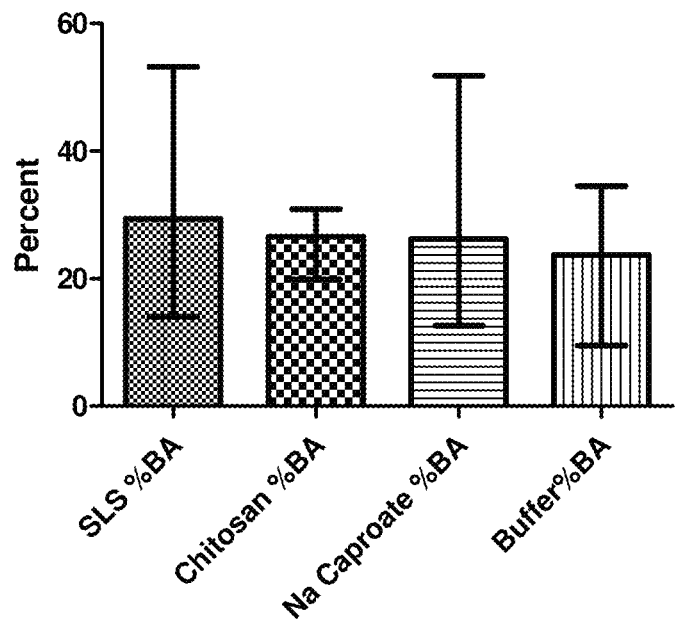
FIG. 11 depicts bioavailability data for various intranasally administered DPH formulations.

The % bioavailability was assessed for IN administration of DPH in buffer alone, as well as DPH in combination with each the three penetration enhancers. Data is provided below in Table 21, where the % bioavailability is calculated by dividing $AUC_{last}$ IN {for buffer and each enhancer} by mean $AUC_{last}$ IV. FIG. 11 depicts a bar plot of the mean values for % bioavailability for DPH administered as an IN formulation with each of the three enhancers as well as buffer. Observed % bioavailability ranges are also depicted in FIG. 11. As shown in both Table 21 and FIG. 11, the mean % bioavailability of the buffer was 23.7%, while the mean % bioavailability for each of the three enhancers was higher than that of buffer and ranged from 26.3% to 29.4%.

TABLE 21

Mean % Bioavailability of DPH Administered IN with Penetration Enhancers or Buffer Relative to IV Administration of DPH in Buffer

| | Sodium Lauryl Sulfate | Chitosan | Sodium Caproate | Buffer |
|---|---|---|---|---|
| Mean | 29.36 | 26.59 | 26.25 | 23.73 |
| St Dev | 16.82 | 4.99 | 17.92 | 11.26 |
| % CV | 57.3 | 18.7 | 68.3 | 47.5 |

Brain tissue from the rat having the highest DPH plasma concentration from each cohort group above was harvested 60 minutes post-administration. These tissue samples were evaluated for the presence of DPH. As shown below in Table 22, clinically relevant DPH concentrations (approached that achieved with intravenous administration) was observed following intranasal administration of DPH.

TABLE 22

Brain Tissue Concentrations (0.357 mg/kg DPH)

| Group # | Route of Administration (Vehicle) | Rat # | Brain Weight (g) | Brain Homogenate Volume (mL) | Brain Homogenate Conc. (ng/mL) | Brain Tissue Conc. (ng/g) | CSF Conc. (ng/mL)* |
|---|---|---|---|---|---|---|---|
| 1 | IV (50 mM Acetate buffer) | 804 | 1.943 | 5.83 | 60.0 | 180 | 10.7 |
| 2 | IN (50 mM Acetate buffer) | 808 | 2.035 | 6.11 | 45.0 | 135 | 6.73 |
| 3 | IN (1% Sodium Caprate/ 50 mM Acetate buffer) | 812 | 1.754 | 5.26 | 34.9 | 105 | 5.21 |
| 4 | IN (0.5% Chitosan oligosaccharide/ 50 mM Acetate buffer) | 817 | 1.925 | 5.78 | 36.4 | 109 | 6.07 |
| 5 | IN (0.5% Sodium Lauryl Sulfate/ 50 mM Acetate buffer) | 818 | 1.883 | 5.65 | 53.1 | 159 | 7.34 |

From the foregoing, it will be appreciated that additional embodiments include but are not limited to the following:

Additional Embodiments

1. A pharmaceutical composition comprising diphenhydramine, or a pharmaceutically acceptable salt thereof, and a liquid vehicle, wherein intranasal administration of the composition provides a $C_{max}$ value that is between 15 ng/mL and 500 ng/mL.
2. The pharmaceutical composition of embodiment 1, wherein intranasal administration of the composition provides a $C_{max}$ value that is between 30 ng/mL and 500 ng/mL.
3. The pharmaceutical composition of embodiment 1 or embodiment 2, wherein intranasal administration of the composition provides a $C_{max}$ value that is between 80 ng/mL and 500 ng/mL.
4. The pharmaceutical composition of embodiment 1 or embodiment 2, wherein intranasal administration of the composition provides a $C_{max}$ value that is between 30 ng/mL and 60 ng/mL.
5. The pharmaceutical composition of any one of embodiments 1-3, wherein intranasal administration of the composition provides a $C_{max}$ value that is between 80 ng/mL and 110 ng/mL.
6. A pharmaceutical composition comprising diphenhydramine, or a pharmaceutically acceptable salt thereof, and a liquid vehicle, wherein intranasal administration of the composition provides a $T_{max}$ value that is less than 10 minutes.
7. A pharmaceutical composition comprising diphenhydramine or a pharmaceutically acceptable salt thereof, and a liquid vehicle, wherein intranasal administration of the composition provides direct administration to the brain and/or cerebrospinal fluid.
8. A method of systemically delivering diphenhydramine, or a pharmaceutically acceptable salt thereof, to a patient in need thereof, the method comprising intranasally administering a pharmaceutical composition comprising diphenhydramine, or a pharmaceutically acceptable salt thereof and a liquid vehicle.
9. The method of embodiment 8, wherein the patient is experiencing an allergic reaction.
10. The method of embodiment 8, wherein the patient is experiencing insomnia.
11. The method of embodiment 8, wherein the patient is experiencing seasonal allergies.
12. The method of embodiment 8, wherein the patient is experiencing a headache or migraine.
13. The method of embodiment 8, wherein the patient is experiencing motion sickness.
14. The method of embodiment 8, wherein the patient is experiencing nausea.
15. The method of embodiment 8, wherein the patient is experiencing extrapyramidal symptoms associated with a neurological disorder.
16. The method of embodiment 8, wherein the patient is experiencing a cough.
17. The method of embodiment 8, wherein the patient is experiencing pain.
18. The method of any one of embodiments 8-17, wherein the intranasally delivering provides a $C_{max}$ value that is between 15 ng/mL and 500 ng/mL.
19. The method of any one of embodiments 8-18, wherein the intranasally delivering provides a $C_{max}$ value that is between 30 ng/mL and 500 ng/mL.
20. The method of any one of embodiments 8-19, wherein the intranasally delivering provides a $C_{max}$ value that is between 80 ng/mL and 500 ng/mL.
21. The method of any one of embodiments 8-19, wherein the intranasally delivering provides a $C_{max}$ value that is between 30 ng/mL and 60 ng/mL.
22. The method of any one of embodiments 8-20, wherein the intranasally delivering provides a $C_{max}$ value that is between 80 ng/mL and 110 ng/mL.
23. A method of directly administering diphenhydramine, or a pharmaceutically acceptable salt thereof, to brain tissue or cerebrospinal fluid, the method comprising intranasally administering pharmaceutical composition comprising diphenhydramine, or a pharmaceutically acceptable salt thereof, and a liquid vehicle.

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

What is claimed is:

1. A method of providing diphenhydramine to a patient in need thereof, the method comprising the steps of:
providing a pharmaceutical composition comprising diphenhydramine hydrochloride or diphenhydramine citrate as the sole active ingredient, at least one penetration enhancer, and an aqueous vehicle, wherein said at least one penetration enhancer is present in an amount ranging from 0.5-2.0% by weight of the composition, and wherein said at least one penetration enhancer is selected from the group consisting of chitosan oligosaccharide, sodium lauryl sulfate, sodium caprate, and combinations thereof; and
wherein the pharmaceutical composition does not include liposomes, propellant, or cyclodextrin;
wherein the dynamic viscosity of the composition, measured at 23° C., is between 5 and 100 cP;
intranasally administering the pharmaceutical composition to the patient,
wherein intranasal administration provides a $C_{max}$ value of diphenhydramine that is at least 20 ng/mL and a $T_{max}$ value of diphenhydramine that is less than or equal to five minutes following administration.

2. The method according to claim 1, wherein the intranasally administering provides a therapeutically effective amount of diphenhydramine to the brain tissue of the patient.

3. The method of claim 1, wherein the patient is experiencing insomnia.

4. The method of claim 1, wherein the patient is experiencing an anaphylactic reaction.

5. The method of claim 1, wherein the pharmaceutical composition has a pH value that is between 4.5 and 6.5.

6. The method of claim 1, wherein the concentration of diphenhydramine in the composition is between 50 milligrams per milliliter (mg/mL) and 150 mg/mL as calculated on the basis of diphenhydramine free base.

7. The method of claim 1, wherein the aqueous vehicle comprises water and at least one other water-soluble solvent.

8. The method of claim 7, wherein the at least one other water-soluble solvent is selected from the group consisting of propylene glycol, glycerin, polyethylene glycol, and combinations thereof.

9. A method of treating anaphylaxis in a patient in need thereof, comprising intranasally administering to the patient a composition comprising:
diphenhydramine hydrochloride or diphenhydramine citrate as the sole active ingredient, at least one penetration enhancer, and an aqueous vehicle, wherein said at least one penetration enhancer is present in an amount ranging from 0.5-2.0% by weight of the composition, and wherein said at least one penetration enhancer is selected from the group consisting of chitosan oligosaccharide, sodium lauryl sulfate, sodium caprate, and combinations thereof; and wherein the pharmaceutical composition does not include liposomes, propellant, or cyclodextrin;
wherein the dynamic viscosity of the composition, measured at 23° C., is between 5 and 100 cP;
intranasally administering the pharmaceutical composition to the patient,
wherein intranasal administration provides a $C_{max}$ value of diphenhydramine that is at least 20 ng/mL and a $T_{max}$ value of diphenhydramine that is less than or equal to five minutes following administration.

10. The method of claim 9, wherein the aqueous composition comprises water and at least one other water-soluble solvent.

11. A method of treating insomnia in a patient in need thereof, comprising intranasally administering to the patient a composition comprising:
diphenhydramine hydrochloride or diphenhydramine citrate as the sole active ingredient, at least one penetration enhancer, and an aqueous vehicle, wherein said at least one penetration enhancer is present in an amount ranging from 0.5-2.0% by weight of the composition, and wherein said at least one penetration enhancer is selected from the group consisting of chitosan oligosaccharide, sodium lauryl sulfate, sodium caprate, and combinations thereof; and wherein the pharmaceutical composition does not include liposomes, propellant, or cyclodextrin;
wherein the dynamic viscosity of the composition, measured at 23° C., is between 5 and 100 cP;
intranasally administering the pharmaceutical composition to the patient,
wherein intranasal administration provides a $C_{max}$ value of diphenhydramine that is at least 20 ng/mL and a $T_{max}$ value of diphenhydramine that is less than or equal to five minutes following administration.

12. The method of claim 11, wherein the aqueous composition comprises water and at least one other water-soluble solvent.

* * * * *